(12) United States Patent
Nakagawa et al.

(10) Patent No.: US 8,835,631 B2
(45) Date of Patent: Sep. 16, 2014

(54) THERAPEUTIC AGENT FOR CEREBRAL INFARCTION

(75) Inventors: Haruto Nakagawa, Osaka (JP); Naoko Ando, Osaka (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 239 days.

(21) Appl. No.: 12/601,609

(22) PCT Filed: May 23, 2008

(86) PCT No.: PCT/JP2008/059582
§ 371 (c)(1),
(2), (4) Date: Nov. 24, 2009

(87) PCT Pub. No.: WO2008/146753
PCT Pub. Date: Dec. 4, 2008

(65) Prior Publication Data
US 2010/0179157 A1    Jul. 15, 2010

(30) Foreign Application Priority Data

May 24, 2007 (JP) .................... 2007-137504

(51) Int. Cl.
| | | |
|---|---|---|
| *C07D 403/04* | (2006.01) |
| *C07D 487/18* | (2006.01) |
| *A61K 31/506* | (2006.01) |
| *A61P 9/10* | (2006.01) |
| *C07D 401/12* | (2006.01) |

(52) U.S. Cl.
CPC ............ *C07D 401/12* (2013.01); *C07D 487/18* (2013.01); *C07D 403/04* (2013.01)
USPC ..................................... 544/295; 514/252.14

(58) Field of Classification Search
USPC ..................................... 544/295; 514/252.14
See application file for complete search history.

(56) References Cited

U.S. PATENT DOCUMENTS

| | | | |
|---|---|---|---|
| 6,455,528 B1 * | 9/2002 | Adachi et al. ............ 514/252.14 |
| 2003/0212080 A1 | 11/2003 | Matasi et al. |
| 2006/0142301 A1 | 6/2006 | Hutchison et al. |
| 2006/0167014 A1 | 7/2006 | Adachi et al. |
| 2007/0232614 A1 | 10/2007 | Fukuda et al. |

FOREIGN PATENT DOCUMENTS

| | | |
|---|---|---|
| EP | 1 029 851 A1 | 8/2000 |
| JP | 2005-511698 | 4/2005 |
| WO | WO99/19301 | 4/1999 |
| WO | 2005/103013 A1 | 11/2005 |
| WO | WO 2007054789 A1 * | 5/2007 |

OTHER PUBLICATIONS

Dirnagl et al., "Pathobiology of ischaemic stroke: an integrated view", Trends in Neurosciences, vol. 22, No. 9, pp. 391-397 (1999).
Dirnagl et al., "Ischemic tolerance and endogenous neuroprotection", Trends in Neurosciences, vol. 26, No. 5, pp. 248-254 (May 2003).
Wang et al., "Inhibition of Tumor Necrosis Factor-α-Converting Enzyme by a Selective Antagonist Protects Brain from Focal Ischemic Injury in Rats", Molecular Pharmacology, vol. 65, No. 4, pp. 890-896 (2004).
Yamasaki et al., "Interleukin-1 as a Pathogenetic Mediator of Ischemic Brain Damage in Rats", Stroke, 26, pp. 676-681 (1995).
Betz et al., "Attenuation of Stroke Size in Rats Using an Adenoviral Vector to Induce Overexpression of Interleukin-1 Receptor Antagonist in Brain", Journal of Cerebral Blood Flow and Metabolism, 15, pp. 547-551 (1995).
Emsley et al., "A randomised phase II study of interleukin-1 receptor antagonist in acute stroke patients", J. Neurol Neurosurg Psychiatry, 76, pp. 1366-1372 (2005).
Fukuda et al., "Treatment with Y-40138, a multiple cytokine production modulator, inhibits lipopolysaccharide- or tumour necrosis factor-α-induced production of pro-inflammatory cytokines and augments interleukin-10", Journal of Pharmacy and Pharmacology, 57, pp. 1461-1466 (2005).
Hisadome et al., "Combination benefit of a pyrimidylpiperazine derivative (Y-40138) and methotrexate in arthritic rats", European Journal of Pharmacology, 497, pp. 351-359 (2004).
Tokushi Hanano, et al. "Novel DMARDs on the Basis of a New Concept of Dual Cytokine Regulation, TNF-x Suppression and IL-10 Augmentation," Bioorganic & Medicinal Chemistry Letters, vol. 10, No. 9, 2000, pp. 881-884.
F.C. Barone Ph. D, et al. "Tumor Necrosis Factor-x: A Mediator of Focal Ischemic Brain Injury," Stroke, http://stroke.adajournals.org/cgi/content/full/28/6/1233, vol. 28, No. 6, Jun. 1997, pp. 1233-1244.
Extended European Search Report issued Oct. 12, 2012, in European Patent Application No. 12182964.2.
Pantoni et al., Arterioscler. Thromb. Vasc. Biol., 18, 503-513, 1995.
Sharp et al., J. Cereb. Blood Flow Metab., 20, 1011-1032, 2000.

* cited by examiner

*Primary Examiner* — Venkataraman Balasubramanian
(74) *Attorney, Agent, or Firm* — Oblon, Spivak, McClelland, Maier & Neustadt, L.L.P.

(57) ABSTRACT

The present invention provides a novel therapeutic drug for cerebral infarction, which contains a piperazine compound as an active ingredient.

The compound of the present invention can be provided as a novel therapeutic drug for cerebral infarction having an effect of suppressing brain injury volume or improving neurological deficit, since it suppresses production of plural inflammatory cytokines and chemokines present in the brain such as TNF-α, IL-1β, IL-6 and MCP-1 and the like.

9 Claims, 4 Drawing Sheets

THERAPEUTIC AGENT FOR CEREBRAL INFARCTION

TECHNICAL FIELD

The present invention relates to a novel therapeutic drug for cerebral infarction.

BACKGROUND ART

The pathology of cerebral ischemia is divided into the hyperacute stage (about 3 hours from the onset) and the acute stage (about 2 weeks from the onset). The cerebral ischemic neuronal cell death is known to relate to excitatory amino acid toxicity and free radical. In the excitatory amino acid toxicity, a cellular disorder is developed in the hyperacute stage due to calcium influx associated with release of glutamic acid caused by energy disorders and binding of the acid to its receptor, and inflammation reaction occurs in the acute stage (non-patent document 1). As for free radical, its increase or hypoxic condition induces expression of an inflammatory gene (proinflammatroy gene) via production of a transcription factor such as transcription Nuclear factor KB (hereinafter NF-κB), Hypoxia-inducible transcription factor-1 (hereinafter HIF-1), Signal transducer and activator of transcription 3 (hereinafter STAT3) and the like (non-patent document 2). Through these mechanisms, inflammatory cytokines such as tumor necrosis factor-α (hereinafter TNF-α), Interleukin-1β (hereinafter IL-1β), interleukin-6 (hereinafter IL-6) and the like are produced. These cytokines are considered to advance symptoms such as brain edema and inflammatory cell infiltration, and encourage neurological deficit.

At present, as a drug showing neuroprotection against ischemia, only Edaravon that traps free radical (hydroxy radical) can be mentioned, which is used for treating cerebral infarction (atherothrombotic brain infarction, lacunar infarction, cardioembolic stroke). On the other hand, although ion channel ($Ca^{2+}$, $Na^+$) inhibitors and glutamic acid receptor inhibitors suppress cerebral infarction in animal experiments, they fail to show effect in clinical trials. Therefore, a neuroprotective agent having novel action mechanisms such as suppression of neuroinflammation and the like, which protects cerebral neuronal cells and suppresses enlargement of ischemic region is expected.

As for the suppression of inflammatory cytokine that has been reported to act neurotoxically in cerebral ischemic pathology, for example, when topical cerebral ischemic disorder of rat is aggravated by the administration of TNF-α in animal experiments, the cerebral ischemic disorder can be alleviated by a intraventricular administration of a TNF-α antibody (non-patent document 3). Moreover, it has been reported that DPH-067517, a TNF-α converting enzyme inhibitor, suppresses TNF-α expression on the cerebral infarction side and reduces neurological deficit and cerebral infarct volume in rat cerebral infarction model (non-patent document 4). In addition, a report has documented that injection of recombinant IL-1β into rat cerebral ventricle increases the cerebral infarction (non-patent document 5), and moreover, a cerebral ischemic disorder alleviating action by the administration of an IL-1β receptor antagonist (recombinant IL-1ra) is shown (non-patent document 6). In the clinical trial (Phase II), moreover, a cerebral ischemic disorder alleviating effect by administration of recombinant IL-1ra has been reported (non-patent document 7). However, there has been no report heretofore on a low-molecular-weight compound having a direct action on the IL-1β molecule per se, and the above-mentioned DPH-067517 cannot suppress the IL-1β expression on the cerebral infarction side.

As mentioned above, while many reports relating to individual inflammatory cytokines and cerebral infarction have been made, the effect thereof is not sufficient.

As a compound that inhibits TNF-α, the present inventors have found piperazine compounds having the properties shown in patent documents 1 and 2. Patent document 1 describes that the compound is effective for various diseases associated with various abnormalities in TNF-α production, TNF-α mediated diseases or diseases treatable with interleukin 10 (IL-10) (transplantation, osteoporosis, myocardial infarction, chronic cardiac failure, cardiac failure, ischemia-reperfusion injury and the like), and patent document 2 describes that the compound is effective for nonviral hepatitis. Moreover, non-patent documents 8 and 9 report that the compound is effective for hepatitis and rheumatoid arthritis models since the compound suppresses production of inflammatory cytokines TNF-α and IL-12 and promotes production of anti-inflammatory cytokine IL-10. However, the effectiveness of the compound for cerebral infarction and its treatment effect on cerebral infarction are not described or suggested.

patent document 1: WO99/19301
patent document 2: WO2005/103013
non-patent document 1: Dirnagl, U. et al., Trends. Neurosci., 22, 391-397 (1999)
non-patent document 2: Dirnagl, U. et al., Trends. Neurosci., 26, 248-254 (2003)
non-patent document 3: Barone, F. C. et al., Stroke, 28, 1223-1244 (1997)
non-patent document 4: Wang, X., et al., Molecular Pharmacology, 65, 890-896 (2004)
non-patent document 5: Yamazaki, Y. et al., Stroke, 26, 676-681 (1995)
non-patent document 6: Betz, A. L. et al., J. Cereb. Blood Flow Metab., 15, 547-551 (1995)
non-patent document 7: Emsley, H. C. A. et al., J. Neurol. Neurosurg. Psych., 76, 1366-1372 (2005)
non-patent document 8: Fukuda, T. et al., J. Pharmacy Pharmacol., 57, 1-6 (2005)
non-patent document 9: Hisadome, M. et al., Eur. J. Pharmacol., 497, 351-359 (2004)

DISCLOSURE OF THE INVENTION

Problems to be Solved by the Invention

The present inventors have found that a certain kind of piperazine compound can be provided as a novel therapeutic drug for cerebral infarction by measuring brain injury volume of monkey middle cerebral artery permanent occlusion model by nuclear magnetic resonance imaging (Magnetic resonance imaging, hereinafter MRI) in the same manner as in clinical measurements and determining the details of neurological function (higher brain function), which resulted in the completion of the present invention. They have also found that the present compound suppresses not only inflammatory cytokines such as TNF-α, IL-12 and interferon γ (hereinafter IFN-γ), but also cytokines and chemokines such as IL-1β, IL-6 and monocyte chemotactic factor (Monocyte chemotactic protein-1, hereinafter MPC-1) and the like. They have further confirmed that the present compound suppresses plural cytokines and chemokines present in the brain such as TNF-α, IL-1β, IL-6 and MPC-1 and the like.

Means of Solving the Problems

Accordingly, the gist of the present invention is as follows.
[1] An agent for treating cerebral infarction, comprising a piperazine compound represented by the formula <1>

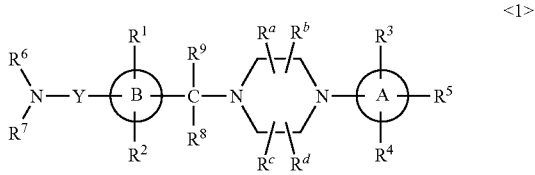

wherein
R$^1$ and R$^2$ are the same or different and each is hydrogen, halogen, lower alkyl, lower alkoxy, amino, amino which is mono- or di-substituted by group(s) selected from lower alkyl and lower acyl, nitro, hydroxy or cyano,
  R$^3$, R$^4$ and R$^5$ are the same or different and each is hydrogen, halogen, lower alkyl, lower alkoxy, nitro, amino, amino which is mono- or di-substituted by group(s) selected from lower alkyl and lower acyl, hydroxy or cyano,
  R$^6$ and R$^7$ are the same or different and each is hydrogen, lower alkyl, lower alkyl substituted by 1 to 3 halogens, aralkyl, acyl or lower acyl substituted by 1 to 3 halogens,
  R$^8$, R$^9$ are the same or different and each is hydrogen or lower alkyl,
  R$^a$-R$^d$ are the same or different and each is hydrogen, lower alkyl, aralkyl or hydroxy lower alkyl, or any two of R$^a$-R$^d$ are bonded to each other to form alkylene having a carbon number of 1 or 2,
  Y is a group represented by the formula

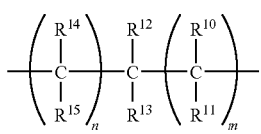

wherein
R$^{10}$ and R$^{11}$ are the same or different and each is hydrogen or lower alkyl,
  R$^{12}$ and R$^{13}$ are the same or different and each is hydrogen or lower alkyl, or R$^{12}$ and R$^{13}$ are groups that form alkylene in combination,
  R$^{14}$ and R$^{15}$ are the same or different and each is hydrogen or lower alkyl, and
  m is an integer of 0-2, n is an integer of 0-2 and 0≤m+n≤2,
  ring A is phenyl, pyrimidyl, thiazolyl, pyridyl, pyradyl pyrazinyl or imidazolyl, and
  ring B is phenyl, pyridyl or thienyl
(hereinafter sometimes to be indicated as the compound of the present invention <1>) or a pharmaceutically acceptable salt thereof as an active ingredient.
[2] The agent of [1], wherein the active ingredient is a compound of the formula <1> wherein the ring B is phenyl, or a pharmaceutically acceptable salt thereof.
[3] The agent of [2], wherein the active ingredient is a compound of the formula <1> wherein
  R$^1$ and R$^2$ are hydrogen,
  R$^3$, R$^4$ and R$^5$ are the same or different and each is hydrogen, halogen or lower alkoxy,
  R$^6$ and R$^7$ are the same or different and each is hydrogen or acyl,
  R$^8$ and R$^9$ are the same or different and each is hydrogen or lower alkyl,
  R$^{10}$ and R$^{11}$ are hydrogen,
  R$^{14}$ and R$^{15}$ are hydrogen,
  R$^a$, R$^b$, R$^c$ and R$^d$ are each hydrogen, or any two are bonded to each other to form alkylene having a carbon number of 1 and other groups are hydrogen,
  ring A is phenyl, pyrimidyl, thiazolyl or pyridyl, and
  ring B is phenyl, or a pharmaceutically acceptable salt thereof.
[4] The agent of [2] above, wherein the active ingredient is at least one selected from the following compounds:
  N-{4-[(4-phenylpiperazin-1-yl)methyl]phenylmethyl}acetamide,
  N-(4-{[4-(4-fluorophenyl)piperazin-1-yl]methyl}phenylmethyl)acetamide,
  N-(4-{[4-(2-fluorophenyl)piperazin-1-yl]methyl}phenylmethyl)acetamide,
  N-(4-{[4-(2,4-difluorophenyl)piperazin-1-yl]methyl}phenylmethyl)acetamide,
  N-(2-{4-[(4-phenylpiperazin-1-yl)methyl]phenyl}ethyl)acetamide,
  N-[2-(4-{[4-(4-fluorophenyl)piperazin-1-yl]methyl}phenyl)ethyl]acetamide,
  N-(1-{4-[(4-phenylpiperazin-1-yl)methyl]phenyl}ethyl)acetamide,
  N-[1-(4-{[4-(4-fluorophenyl)piperazin-1-yl]methyl]phenyl)ethyl}acetamide,
  N-[1-(4-{[4-(2,4-difluorophenyl)piperazin-1-yl]methyl}phenyl)ethyl]acetamide,
  N-[1-(4-{[4-(4-fluorophenyl)piperazin-1-yl]methyl}phenyl)-1-methylethyl]acetamide,
  N-(1-{4-[(4-phenylpiperazin-1-yl)methyl]phenyl}cyclopropyl)acetamide,
  N-[1-(4-{[4-(4-fluorophenyl)piperazin-1-yl]methyl}phenyl)cyclopropyl]acetamide, etamide,
  N-{4-[1-(4-phenylpiperazin-1-yl)ethyl]phenylmethyl}acetamide,
  N-(4-{1-[4-(4-fluorophenyl)piperazin-1-yl]ethyl}phenylmethyl)acetamide,
  N-(4-{1-[4-(2,4-difluorophenyl)piperazin-1-yl]ethyl}phenylmethyl)acetamide,
  N-(4-{1-[4-(4-fluorophenyl)piperazin-1-yl]-1-methylethyl}phenylmethyl)acetamide,
  N-(4-{1-[4-(4-fluorophenyl)piperazin-1-yl]-1-methylethyl}phenylmethyl)acetamide,
  N-(1-(4-((4-(pyrimidin-2-yl)piperazin-1-yl)methyl)phenyl)cyclopropyl)acetamide, and
  N-[1-(4-{[(1S,4S)-5-(pyrimidin-2-yl)-2,5-diazabicyclo[2.2.1]hept-2-yl]methyl}phenyl)cyclopropyl]acetamide,
  or a pharmaceutically acceptable salt thereof.
[5] The agent of [1], wherein the active ingredient is a compound of the formula <1> wherein ring B is pyridyl, or a pharmaceutically acceptable salt thereof
[6] The agent of [5], wherein the active ingredient is a compound of the formula <1> wherein
  R$^1$ and R$^2$ are hydrogen,
  R$^3$, R$^4$ and R$^5$ are the same or different and each is hydrogen, halogen or lower alkoxy,
  R$^6$ and R$^7$ are the same or different and each is hydrogen or acyl,
  R$^8$ and R$^9$ are the same or different and each is hydrogen or lower alkyl,
  R$^{10}$ and R$^{11}$ are hydrogen,
  R$^{14}$ and R$^{15}$ are hydrogen, $R^a$, $R^b$, $R^c$ and $R^d$ are each hydrogen, or any two are bonded to each other to form alkylene having a carbon number of 1 group and other groups are each hydrogen,
  ring A is phenyl, pyrimidyl, thiazolyl or pyridyl, and ring B is pyridyl,
or a pharmaceutically acceptable salt thereof.

[7] The agent of [5], wherein the active ingredient is at least one selected from the following compounds:
  N-(1-{5-[{4-(pyrimidin-2-yl)piperazin-1-yl}methyl]pyridin-2-yl}cyclopropyl)acetamide, and
  N-[1-(5-{[(1S,4S)-5-(pyrimidin-2-yl)-2,5-diazabicyclo[2.2.1]hept-2-yl]methyl}pyridin-2-yl)cyclopropyl]acetamide,
  or a pharmaceutically acceptable salt thereof.

[8] The agent of [1], wherein the active ingredient is a compound of the formula <1> wherein $R^{12}$ and $R^{13}$ are groups that form alkylene in combination, or a pharmaceutically acceptable alt thereof.

[9] The agent of [8], wherein the active ingredient is at least one selected from the following compounds:
  N-(1-{4-[(4-phenylpiperazin-1-yl)methyl]phenyl}cyclopropyl)acetamide,
  N-[1-(4-{[4-(4-fluorophenyl)piperazin-1-yl]methyl}phenyl)cyclopropyl]acetamide, etamide,
  N-[1-(4-{1-[4-(pyrimidin-2-yl)piperazin-1-yl]ethyl}phenyl)cyclopropyl]acetamide,
  N-[1-(4-{[(1S,4S)-5-(pyrimidin-2-yl)-2,5-diazabicyclo[2.2.1]hept-2-yl]methyl}phenyl)cyclopropyl]acetamide,
  N-(1-{5-[{4-(pyrimidin-2-yl)piperazin-1-yl}methyl]pyridin-2-yl}cyclopropyl)acetamide, and
  N-[1-(5-{[(1S,4S)-5-(pyrimidin-2-yl)-2,5-diazabicyclo[2.2.1]hept-2-yl]methyl}pyridin-2-yl)cyclopropyl]acetamide,
  or a pharmaceutically acceptable salt thereof.

[10] The agent of [2] or [8] above, wherein the active ingredient is N-[1-(4-{1-[4-(pyrimidin-2-yl)piperazin-1-yl]ethyl}phenyl)cyclopropyl]acetamide or a pharmaceutically acceptable salt thereof.

[11] The agent of [2] or [8] above, wherein the active ingredient is N-[1-(4-{1-[4-(pyrimidin-2-yl)piperazin-1-yl]ethyl}phenyl)cyclopropyl]acetamide hydrochloride.

[12] The agent of [1], wherein the cerebral infarction is atherothrombotic brain infarction, lacunar infarction or cardioembolic stroke.

[13] A piperazine compound represented by the formula <2>

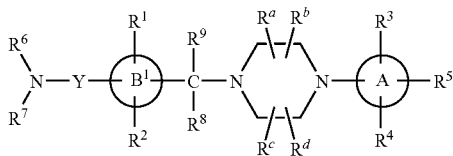

wherein
  $R^1$ and $R^2$ are the same or different and each is hydrogen, halogen, lower alkyl, lower alkoxy, amino, amino which is mono- or di-substituted by group(s) selected from lower alkyl and lower acyl, nitro, hydroxy or cyano,
  $R^3$, $R^4$ and $R^5$ are the same or different and each is hydrogen, halogen, lower alkyl, lower alkoxy, nitro, amino, amino which is mono- or di-substituted by group(s) selected from lower alkyl and lower acyl, hydroxy or cyano, $R^6$ and $R^7$ are the same or different and each is hydrogen, lower alkyl, lower alkyl substituted by 1 to 3 halogens, aralkyl, acyl or lower acyl substituted by 1 to 3 halogens,
  $R^8$ and $R^9$ are the same or different and each is hydrogen or lower alkyl,
  $R^a$-$R^d$ are the same or different and each is hydrogen, lower alkyl, aralkyl or hydroxy lower alkyl, or any two of $R^a$-$R^d$ are bonded to each other to form alkylene having a carbon number of 1-2,
  Y is a group represented by the formula

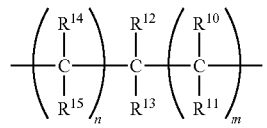

wherein
  $R^{10}$ and $R^{11}$ are the same or different and each is hydrogen or lower alkyl,
  $R^{12}$ and $R^{13}$ are the same or different and each is hydrogen or lower alkyl, or R12 and R13 are groups that form alkylene in combination,
  $R^{14}$ and $R^{15}$ are the same or different and each is hydrogen or lower alkyl,
  m is an integer of 0-2, n is an integer of 0-2, and $0 \leq m+n \leq 2$,
  ring A is phenyl, pyrimidyl, thiazolyl, pyridyl, pyrazinyl or imidazolyl, and
  ring $B^1$ is pyridyl or thienyl,
or a pharmaceutically acceptable salt thereof.

[14] A piperazine compound represented by the formula <3>

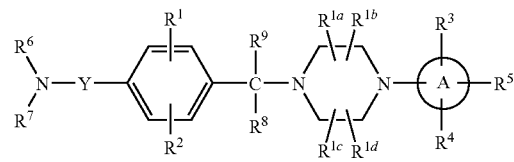

wherein
  $R^1$ and $R^2$ are the same or different and each is hydrogen, halogen, lower alkyl, lower alkoxy, amino, amino which is mono- or di-substituted by group(s) selected from lower alkyl and lower acyl, nitro, hydroxy or cyano,
  $R^3$, $R^4$ and $R^5$ are the same or different and each is hydrogen, halogen, lower alkyl, lower alkoxy, nitro, amino, amino which is mono- or di-substituted by group(s) selected from lower alkyl and lower acyl, hydroxy or cyano,
  $R^6$ and $R^7$ are the same or different and each is hydrogen, lower alkyl, lower alkyl substituted by 1 to 3 halogens, aralkyl, acyl or lower acyl substituted by 1 to 3 halogens,
  $R^8$ and $R^9$ are the same or different and each is hydrogen or lower alkyl,
  at least one of $R^{1a}$-$R^{1d}$ is lower alkyl, aralkyl or hydroxy lower alkyl, or any two of $R^{1a}$-$R^{1d}$ are bonded to each other to form alkylene having a carbon number of 1-2, and other substituents are the same or different and each is hydrogen, lower alkyl, aralkyl or hydroxy lower alkyl, Y is a group represented by the formula

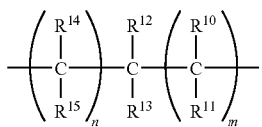

wherein $R^{10}$ and $R^{11}$ are the same or different and each is hydrogen or lower alkyl, $R^{12}$ and $R^{13}$ are the same or different and each is hydrogen or lower alkyl, or $R^{12}$ and $R^{13}$ are groups that form alkylene in combination, $R^{14}$ and $R^{15}$ are the same or different and each is hydrogen or lower alkyl, m is an integer of 0-2, n is an integer of 0-2, and $0 \leq m+n \leq 2$, and ring A is phenyl, pyrimidyl, thiazolyl, pyridyl, pyrazinyl or imidazolyl, or a pharmaceutically acceptable salt thereof.

[15] The piperazine compound of [13], which is represented by the formula <4>

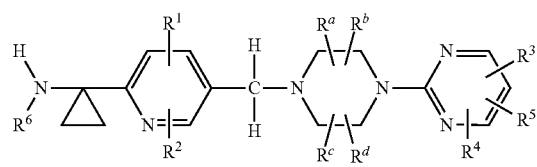

wherein $R^1$ and $R^2$ are the same or different and each is hydrogen, halogen, lower alkyl, lower alkoxy, amino, amino which is mono- or di-substituted by group(s) selected from lower alkyl and lower acyl, nitro, hydroxy or cyano, $R^3$, $R^4$ and $R^5$ are the same or different and each is hydrogen, halogen, lower alkyl, lower alkoxy, nitro, amino, amino which is mono- or di-substituted by group(s) selected from lower alkyl and lower acyl, hydroxy or cyano, $R^6$ is acyl or lower acyl substituted by 1 to 3 halogens, and $R^a$-$R^d$ are the same or different and each is hydrogen, lower alkyl, aralkyl or hydroxy lower alkyl, or any two of $R^a$-$R^d$ are bonded to each other to form alkylene having a carbon number of 1-2, or a pharmaceutically acceptable salt thereof

[16] The piperazine compound of [14], which is represented by the formula <5>

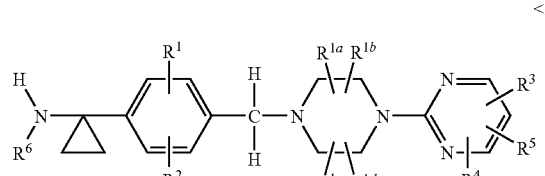

wherein $R^1$ and $R^2$ are the same or different and each is hydrogen, halogen, lower alkyl, lower alkoxy, amino, amino which is mono- or di-substituted by group(s) selected from lower alkyl and lower acyl, nitro, hydroxy or cyano, $R^3$, $R^4$ and $R^5$ are the same or different and each is hydrogen, halogen, lower alkyl, lower alkoxy, nitro, amino, amino which is mono- or di-substituted by alkyl and lower acyl, hydroxy or cyano, $R^6$ is acyl or lower acyl substituted by 1 to 3 halogens, and at least one of $R^{1a}$-$R^{1d}$ is lower alkyl, aralkyl or hydroxy lower alkyl, or any two of $R^{1a}$-$R^{1d}$ are bonded to each other to form alkylene having a carbon number of 1-2, and other substituents are the same or different and each is hydrogen, lower alkyl, aralkyl or hydroxy lower alkyl, or a pharmaceutically acceptable salt thereof.

[17] The piperazine compound of [14] or [16], which is selected from

N-(1-{4-[(3,5-dimethyl-4-pyrimidin-2-ylpiperazin-1-yl)methyl]phenyl}cyclopropyl)acetamide, N-[1-(4-{[(3S)-3-methyl-4-pyrimidin-2-ylpiperazin-1-yl]methyl}phenyl)cyclopropyl]acetamide, N-[1-(4-{[(1S,4S)-5-(pyrimidin-2-yl)-2,5-diazabicyclo[2.2.1]hept-2-yl]methyl}phenyl)cyclopropyl]acetamide, N-(1-{4-[{2,5-dimethyl-4-(pyrimidin-2-yl)}piperazin-1-yl)methyl]phenyl}cyclopropyl)acetamide, N-[1-(4-{[((2R)-2-methyl-4-(pyrimidin-2-yl))piperazin-1-yl]methyl}phenyl)cyclopropyl]acetamide and N-(1-{4-[{(2,6-dimethyl-4-(pyrimidin-2-yl))piperazin-1-yl}methyl]phenyl}cyclopropyl)acetamide, or a pharmaceutically acceptable salt thereof, or the piperazine compound of [13] or [15], which is selected from N-(1-{5-[{4-(pyrimidin-2-yl)piperazin-1-yl}methyl]pyridin-2-yl}cyclopropyl)acetamide and N-[1-(5-{[(1S,4S)-5-(pyrimidin-2-yl)-2,5-diazabicyclo[2.2.1]hept-2-yl]methyl}pyridin-2-yl)cyclopropyl]acetamide, or a pharmaceutically acceptable salt thereof.

Effect of the Invention

The compounds of the formula <1> are useful as a therapeutic drug for cerebral infarction. These compounds suppress inflammatory cytokines and chemokines such as TNF-α, IL-1β, IL-6, MCP-1 and the like, whose production is enhanced in the brain. Moreover, these compounds decrease brain injury volume and improve higher neurological function in monkey middle cerebral artery permanent occlusion model.

BEST MODE FOR CARRYING OUT THE INVENTION

Figure 1:
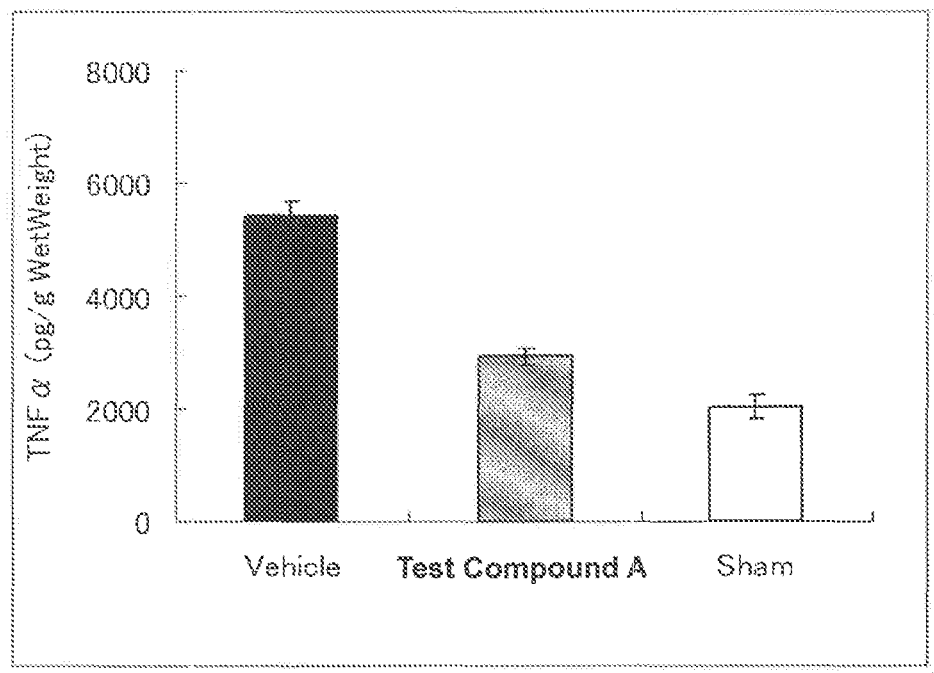
FIG. 1 shows intracerebral TNF-α concentration of rat middle cerebral artery occlusion-reperfusion model, wherein "Sham" is a sham operation group without occlusion with suture, "Vehicle" is a group that was subjected to occlusion and administered with saline alone, and "test compound A" is a test compound A administration group.
Figure 2:
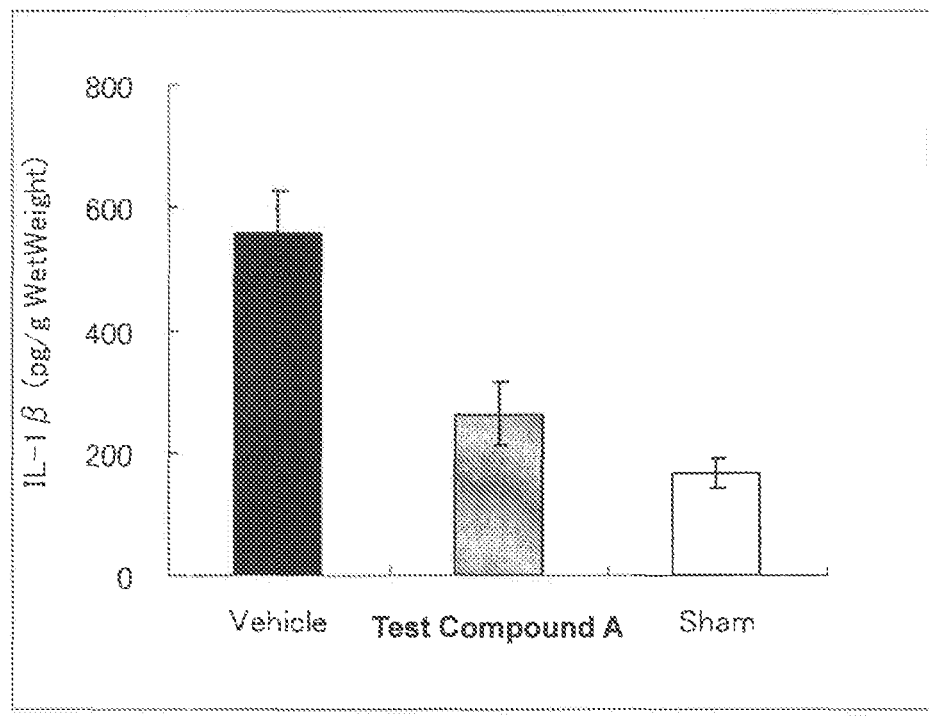
FIG. 2 shows intracerebral IL-1β concentration of rat middle cerebral artery occlusion-reperfusion model, wherein each column means the same as in FIG. 1.
Figure 3:
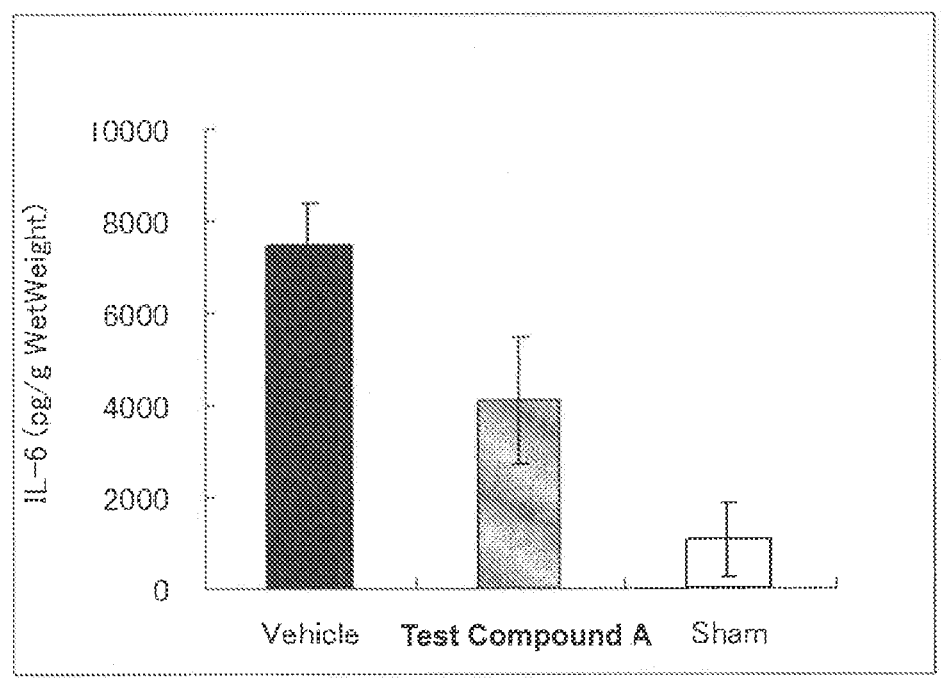
FIG. 3 shows intracerebral IL-6 concentration of rat middle cerebral artery occlusion-reperfusion model, wherein each column means the same as in FIG. 1.
Figure 4:
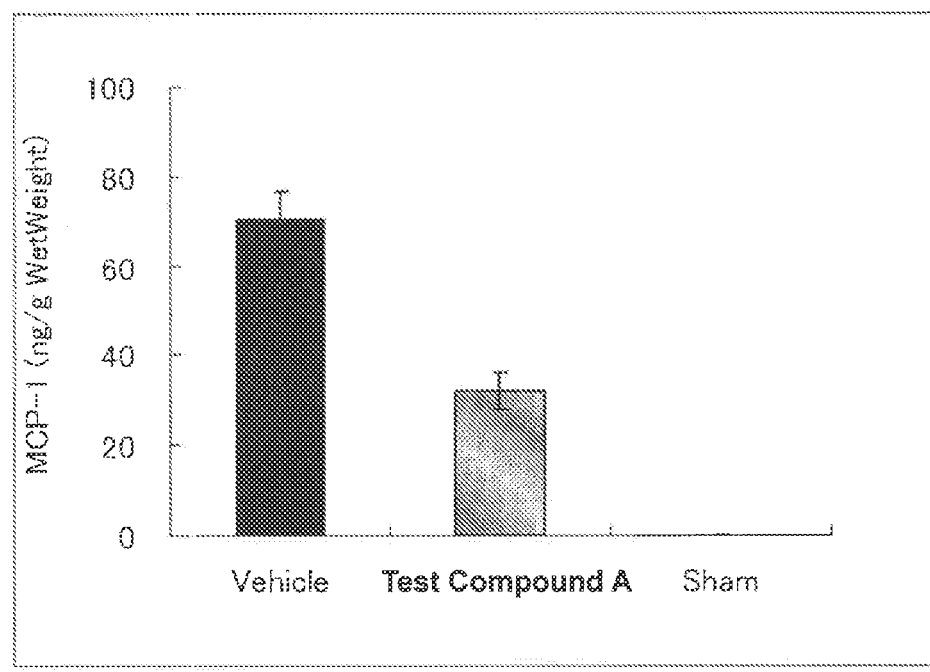
FIG. 4 shows intracerebral MPC-1 concentration of rat middle cerebral artery occlusion-reperfusion model, wherein each column means the same as in FIG. 1.

The present invention is explained in more detail in the following.

The therapeutic drug of the present invention contains a compound represented by the aforementioned formula <1> as an active ingredient. Each symbol in the aforementioned formula <1> means as follows.

The halogen for $R^1$ or $R^2$ is fluorine, chlorine, bromine or iodine.

The lower alkyl for $R^1$ or $R^2$ is alkyl having a carbon number of 1-4, such as methyl, ethyl, propyl, isopropyl, butyl, isobutyl, tertiary butyl and the like.

The lower alkoxy for $R^1$ or $R^2$ is alkoxy having a carbon number of 1-4, such as methoxy, ethoxy, propoxy, isopropoxy, butoxy, tertiary butoxy and the like.

In amino for $R^1$ or $R^2$, which is mono- or di-substituted by a group selected from lower alkyl and lower acyl, lower alkyl as the substituent means alkyl having a carbon number of 1-4, such as methyl, ethyl, propyl, isopropyl, butyl, isobutyl, tertiary butyl and the like. The lower acyl as the substituent means lower alkanoyl having a carbon number of 1-4, which is lower alkanoyl substituted by lower alkoxycarbonyl or phenyl group, such as formyl, acetyl, propionyl, butyryl, methoxycarbonyl, ethoxycarbonyl, propoxycarbonyl, isopropoxycarbonyl, butoxycarbonyl, isobutoxycarbonyl, tertiary butoxycarbonyl, benzoyl, phenylacetyl and phenylpropionyl. Amino mono- or di-substituted by these substituents is methylamino, dimethylamino, ethylamino, diethylamino, propylamino, butylamino, acetylamino, diacetylamino, propionylamino, dipropionylamino, butyrylamino, N-methyl-N-acetylamino, N-ethyl-N-acetylamino, N-methyl-N-propionylamino, methoxycarbonylamino, ethoxycarbonylamino, propoxycarbonylamino, tertiary butoxycarbonylamino, benzoylamino, phenylacetylamino or the like.

The halogen for $R^3$, $R^4$ or $R^5$ is fluorine, chlorine, bromine or iodine.

The lower alkyl for $R^3$, $R^4$ or $R^5$ is alkyl having a carbon number of 1-4, such as methyl, ethyl, propyl, isopropyl, butyl, isobutyl, tertiary butyl and the like.

The lower alkoxy for $R^3$, $R^4$ or $R^5$ is alkoxy having a carbon number of 1-4, such as methoxy, ethoxy, propoxy, isopropoxy, butoxy, tertiary butoxy and the like.

In amino for $R^3$, $R^4$ or $R^5$, which is mono- or di-substituted by a group selected from lower alkyl and lower acyl, lower alkyl as the substituent means alkyl having a carbon number of 1-4, such as methyl, ethyl, propyl, isopropyl, butyl, isobutyl, tertiary butyl and the like. The lower acyl as the substituent means lower alkanoyl having a carbon number of 1-4 or lower alkanoyl substituted by lower alkoxycarbonyl or phenyl group, such as formyl, acetyl, propionyl, butyryl, methoxycarbonyl, ethoxycarbonyl, propoxycarbonyl, isopropoxycarbonyl, butoxycarbonyl, isobutoxycarbonyl, tertiary butoxycarbonyl, benzoyl, phenylacetyl and phenylpropionyl. Amino mono- or di-substituted by these substituents is methylamino, dimethylamino, ethylamino, diethylamino, propylamino, butylamino, acetylamino, diacetylamino, propionylamino, dipropionylamino, butyrylamino, N-methyl-N-acetylamino, N-ethyl-N-acetylamino, N-methyl-N-propionylamino, methoxycarbonylamino, ethoxycarbonylamino, propoxycarbonylamino, tertiary butoxycarbonylamino, benzoylamino, phenylacetylamino or the like.

The lower alkyl for $R^6$ or $R^7$ is alkyl having a carbon number of 1-4, such as methyl, ethyl, propyl, isopropyl, butyl, isobutyl, tertiary butyl and the like.

The lower alkyl substituted by 1 to 3 halogens for $R^6$ or $R^7$ is lower alkyl having a carbon number of 1-4, which is substituted by halogen (fluorine, chlorine, bromine and the like), such as fluoromethyl, trifluoromethyl, chloromethyl, bromomethyl, 2-fluoroethyl, 2,2,2-trifluoroethyl, 2-chloroethyl, 2-bromoethyl, 3-fluoropropyl, 3-chloropropyl, 4-fluorobutyl, 4-chlorobutyl and the like.

The aralkyl for $R^6$ or $R^7$ is benzyl, 2-phenylethyl, 3-phenylpropyl and the like.

The acyl for $R^6$ or $R^7$ is lower alkanoyl having a carbon number of 1-4 or lower alkylsulfonyl having a carbon number of 1-4, which is substituted by alkanoyl having a carbon number of 1-5, lower alkoxycarbonyl having a carbon number of 1-4, phenyl group or pyridyl group, such as formyl, acetyl, propionyl, butyryl, valeryl, isovaleryl, trimethylacetyl, methoxycarbonyl, ethoxycarbonyl, propoxycarbonyl, isopropoxycarbonyl, butoxycarbonyl, isobutoxycarbonyl, tertiary butoxycarbonyl, benzoyl, nicotinoyl, isonicotinoyl, picolinoyl, phenylacetyl, phenylpropionyl, methanesulfonyl and the like.

The lower acyl substituted by 1 to 3 halogens for $R^6$ or $R^7$ is lower acyl having a carbon number of 1-4, which is substituted by halogen (fluorine, chlorine, bromine and the like), such as fluoroacetyl, trifluoroacetyl, chloroacetyl, bromoacetyl, 3-chloropropionyl, 3-bromopropionyl, 4-chlorobutyryl, 4-bromobutyryl and the like.

The lower alkyl for $R^8$ or $R^9$ is alkyl having a carbon number of 1-4, such as methyl, ethyl, propyl, isopropyl, n-butyl, isobutyl, secondary butyl, tertiary butyl and the like.

The lower alkyl for $R^a$, $R^b$, $R^c$ or $R^d$ is alkyl having a carbon number of 1-4, such as methyl, ethyl, propyl, isopropyl, n-butyl, isobutyl, secondary butyl, tertiary butyl and the like.

The aralkyl for $R^a$, $R^b$, $R^c$ or $R^d$ is benzyl, 2-phenylethyl, 3-phenylpropyl or the like.

The lower alkyl of hydroxy lower alkyl for $R^a$, $R^b$, $R^c$ or $R^d$ is alkyl having a carbon number of 1-4, such as methyl, ethyl, propyl, isopropyl, n-butyl, isobutyl, secondary butyl, tertiary butyl and the like.

Any two groups of $R^a$, $R^b$, $R^c$ and $R^d$ that are bonded to each other to form alkylene having a carbon number of 1 or 2 are methylene, ethylene and the like.

The lower alkyl for $R^{10}$ or $R^{11}$ is alkyl having a carbon number of 1-4, such as methyl, ethyl, propyl, isopropyl, butyl and the like.

The lower alkyl for $R^{12}$ or $R^{13}$ is alkyl having a carbon number of 1-4, such as methyl, ethyl, propyl, isopropyl, butyl and the like.

The groups for $R^{12}$ and $R^{13}$ that form alkylene in combination are methylene, ethylene, trimethylene, tetramethylene, pentamethylene and the like.

The lower alkyl for $R^{14}$ or $R^{15}$ is alkyl having a carbon number of 1-4, such as methyl, ethyl, propyl, isopropyl, butyl and the like.

The pyrimidyl, thiazolyl, pyridyl, pyrazinyl and imidazolyl for ring A are 2-pyrimidyl, 4-pyrimidyl, 5-pyrimidyl, 2-thiazolyl, 4-thiazolyl, 5-thiazolyl, 2-pyridyl, 3-pyridyl, 4-pyridyl, 2 pyrazinyl and 2-imidazolyl and the like.

The pyridyl and thienyl for ring B are 2-pyridyl, 3-pyridyl, 4-pyridyl, 2-thienyl, 3-thienyl and the like.

The lower alkyl for $R^{1a}$, $R^{1b}$, $R^{1c}$ or $R^{1d}$ is alkyl having a carbon number of 1-4, such as methyl, ethyl, propyl, isopropyl, n-butyl, isobutyl, secondary butyl, tertiary butyl and the like.

The aralkyl for $R^{1a}$, $R^{1b}$, $R^{1c}$ or $R^{1d}$ is benzyl, 2-phenylethyl, 3-phenylpropyl or the like.

The lower alkyl of hydroxy lower alkyl for $R^{1a}$, $R^{1b}$, $R^{1c}$ or $R^{1d}$ is alkyl having a carbon number of 1-4, such as methyl, ethyl, propyl, isopropyl, n-butyl, isobutyl, secondary butyl, tertiary butyl and the like.

Any two groups of $R^{1a}$, $R^{1b}$, $R^{1c}$ and $R^{1d}$ that are bonded to each other to form alkylene having a carbon number of 1 or 2 are methylene, ethylene and the like.

Particularly, a compound of the formula <1>, wherein $R^1$ and $R^2$ are hydrogens, $R^3$, $R^4$ and $R^5$ are the same or different and each is hydrogen, halogen or lower alkoxy, $R^6$ and $R^7$ are the same or different and each is hydrogen or acyl, $R^8$ and $R^9$ are the same or different and each is hydrogen or lower alkyl, $R^{10}$ and $R^{11}$ are hydrogens, $R^{14}$ and $R^{15}$ are hydrogen, $R^a$, $R^b$, $R^c$ and $R^d$ are hydrogens, or any two are bonded to each other to form alkylene having a carbon number of 1 group and other groups are each hydrogen, ring A is phenyl, pyrimidyl, thiazolyl or pyridyl, and ring B is phenyl or pyridyl, or a pharmaceutically acceptable salt thereof is preferable.

Particularly desired is the above-mentioned compound wherein $R^a$, $R^b$, $R^c$ and $R^d$ are each hydrogen, ring B is phenyl, or a pharmaceutically acceptable salt thereof.

Examples of the pharmaceutically acceptable salt of the compound <1> of the present invention include salts with inorganic acids such as hydrochloric acid, hydrobromic acid, hydroiodic acid, sulfuric acid, nitric acid, phosphoric acid and the like, salts with organic acids such as acetic acid, maleic acid, fumaric acid, benzoic acid, citric acid, succinic acid, tartaric acid, malic acid, mandelic acid, methanesulfonic acid, benzenesulfonic acid, p-toluenesulfonic acid, 10-camphorsulfonic acid and the like, and the like. In addition, the compound <1> of the present invention can be converted to a quaternary ammonium salt. The compound <1> of the present invention or a pharmaceutically acceptable salt thereof may be hydrate (1 hydrate, 1/2 hydrate, 1/4 hydrate, 1/5 hydrate, 2 hydrate, 3/2 hydrate, 3/4 hydrate and the like) or solvate. When the compound <1> of the present invention has an asymmetric atom, at least two kinds of optical isomers are present. Such optical isomers and racemates thereof are also encompassed in the present invention.

Examples of preferable specific compound include the compounds described in [4], [7], [9], [10], [11] and [17] of the above-mentioned gist of the present invention or a pharmaceutically acceptable salt thereof.

Examples of particularly preferable compound include N-[1-(4-{[4-(pyrimidin-2-yl)piperazin-1-yl]methyl}phenyl)cyclopropyl]acetamide or a pharmaceutically acceptable salt thereof, N-[1-(4-{[(1S,4S)-5-(pyrimidin-2-yl)-2,5-diazabicyclo[2.2.1]hept-2-yl]methyl}phenyl)cyclopropyl]acetamide or a pharmaceutically acceptable salt thereof, and N-(1-{5-[{4-(pyrimidin-2-yl)piperazin-1-yl}methyl]pyridin-2-yl}cyclopropyl)acetamide or a pharmaceutically acceptable salt thereof. Among these, N-[1-(4-{[4-(pyrimidin-2-yl)piperazin-1-yl]methyl}phenyl)cyclopropyl]acetamide hydrochloride, N-[1-(4-{[(1S,4S)-5-(pyrimidin-2-yl)-2,5-diazabicyclo[2.2.1]hept-2-yl]methyl}phenyl)cyclopropyl] acetamide hydrochloride, and N-(1-{5-[{4-(pyrimidin-2-yl)piperazin-1-yl}methyl]pyridin-2-yl}cyclopropyl)acetamide hydrochloride are preferable.

A part of the above-mentioned compounds can be produced according to the method described in WO99/19301 (hereinafter patent document 1), and specific Synthetic Examples of the compounds recited above as preferable compounds are included and can be referred to. They can also be synthesized by the following methods, but the methods are not limited thereto.

1) Among the compounds of the present invention, compound <1> wherein ring B is phenyl and any of $R^a$-$R^d$ is hydrogen can be produced according to the method described in patent document 1.

Among the compounds of the present invention, compound wherein ring B is phenyl and at least one of $R^a$-$R^d$ is other than hydrogen can be produced, for example, by a method comprising replacing compound III in method A described in patent document 1 with compound <5-1> (method A-a), or a method similar to method K described in patent document 1 (method K-a).

(Method A-a)

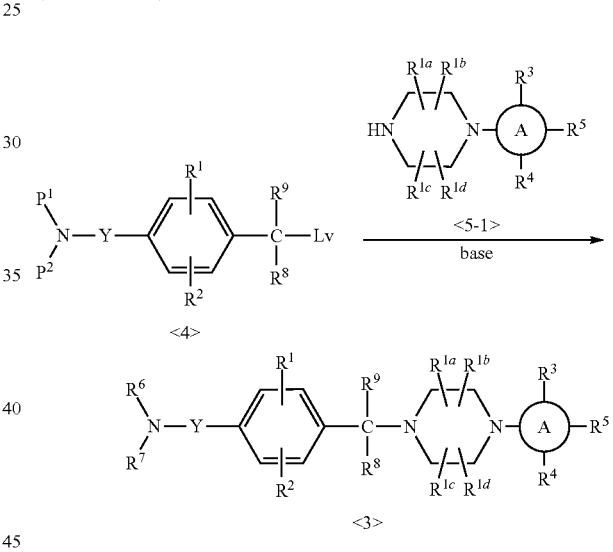

wherein compound <4> is similar to compound (II) described in patent document 1, Lv is a leaving group widely used in the field of organic synthetic chemistry, such as halogen (fluorine, chlorine, bromine, iodine), methanesulfonyloxy, p-toluenesulfonyloxy or trifluoromethanesulfonyloxy, $P^1$ and $P^2$ include $R^6$ and $R^7$ defined above, or an amino-protecting group widely used in the field of organic synthetic chemistry, such as benzyloxycarbonyl group or tert-butyloxycarbonyl group, $P^1$ and $P^2$ optionally form an imide group (e.g., phthalimide and the like) together with the adjacent nitrogen atom, and other symbols are as defined above, provided that when $R^3$, $R^4$, $R^5$, $R^{1a}$, $R^{1b}$, $R^{1c}$ and $R^{1d}$ each have a functional group, they may be protected as necessary.

The condensation reaction of compound <4> and compound <5-1> can be performed in the same manner as in Method A described in patent document 1. As compound <5-1>, a commercially available product is used or can be synthesized from, for example, commercially available piperazine derivative <6-1> according to (Method A-a-1) shown in the following.

(Method A-a-1)

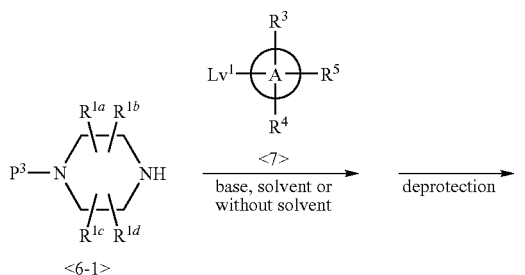

<6-1>

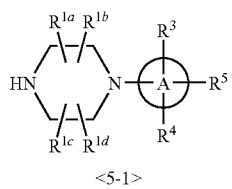

<5-1> wherein $P^3$ is an amino-protecting group widely used in the field of organic synthetic chemistry, such as tert-butyloxycarbonyl group and benzyloxycarbonyl group, $Lv^1$ is a leaving group widely used in aromatic nucleophilic substitution reaction, halogen (fluorine, chlorine, bromine, iodine), methanesulfonyloxy, p-toluenesulfonyloxy, trifluoromethanesulfonyloxy, benzenesulfophenyl, benzenesulfonyloxy, benzenesulfonyl, azido, aryloxy, alkoxy, alkylthio or amino, and other symbols are as defined above]

The condensation reaction of compound <6-1> and compound <7> can be performed in the same manner as in Method K described in patent document 1 or a method described in patent document 1 (Method DD), wherein compound (III) is directly obtained from compound (XLII). Deprotection can be performed by a general deprotection of amino group described in a literature, for example, Protective groups in organic synthesis, John Willey & Sons, INC. (hereinafter non-patent document 10) and the like. In addition, as compound <6-1>, a commercially available product is used or can be synthesized by, for example, protecting an amino group of a commercially available piperazine derivative with a suitable protecting group by a method described in a literature, for example, non-patent document 10 and the like.

(Method K-a)

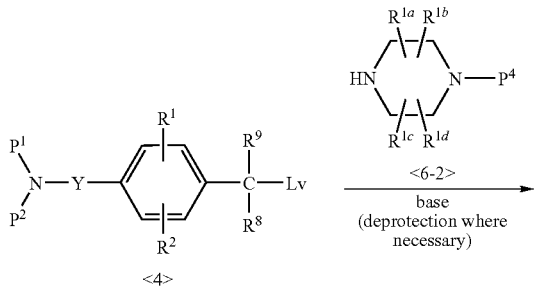

<4> wherein $P^4$ is a hydrogen atom or an amino-protecting group widely used in the field of organic synthetic chemistry, such as tert-butyloxycarbonyl group and benzyloxycarbonyl group, and other symbols are as defined above.

The condensation reaction of compound <4> and compound <6-2> can be performed in the same manner as in Method K described in patent document 1 or a method in described in patent document 1 (Method DD), wherein compound (III) is directly obtained from compound (XLII). When $P^4$ is a protecting group, deprotection is performed by the method described in non-patent document 10 etc., whereby compound <8> is obtained. Compound <8> is reacted with compound <7> under conditions similar to those described in patent document 1, Method K, whereby compound <3> is obtained. As compound <6-2>, a commercially available product is used or can be synthesized by, for example, protecting an amino group of a commercially available piperazine derivative with a suitable protecting group by a method described in a literature, for example, non-patent document 10 and the like.

2) Among the compounds of the present invention, compound <1> wherein ring B is pyridyl or thienyl can be synthesized by, for example, a method similar to Method A described in patent document 1 (Method A-b).

(Method A-b)

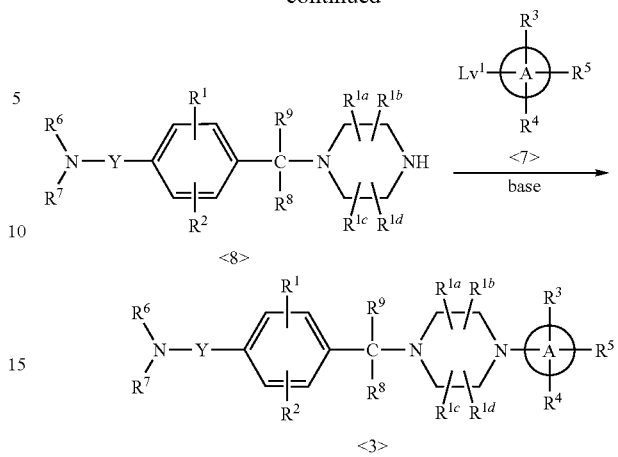

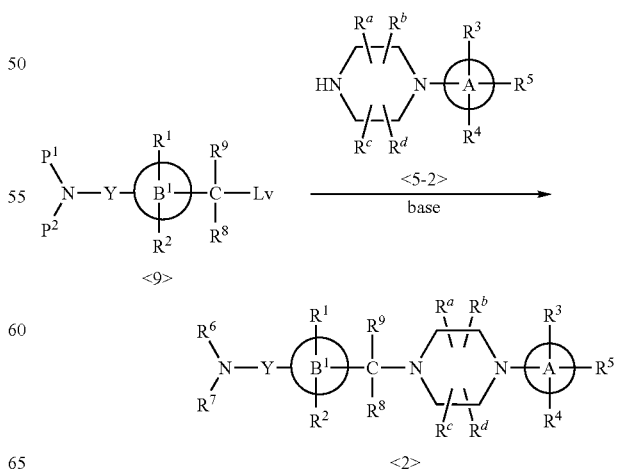

wherein ring $B^1$ is pyridyl or thienyl, and other symbols are as defined above.

The condensation reaction of compound <9> and compound <5-2> can be performed in the same manner as in Method A described in patent document 1. Like <5-1>, compound <5-2> may be a commercially available product, or can be synthesized from a commercially available piperazine derivative by a method similar to, for example, (Method A-a-1).

3) Among the compounds of the present invention, compound <1> wherein ring B is pyridyl or thienyl, m=n=0, $R^{12}$ and $R^{13}$ are groups that form ethylene in combination, one of $R^6$ and $R^7$ is hydrogen and the other is an acetyl group, and $R^8$ and $R^9$ are hydrogens, namely, compound <17> can be synthesized by, for example, a method similar to Method A described in patent document 1 after synthesizing compound <16> by the following method.

(Method A-b-1)

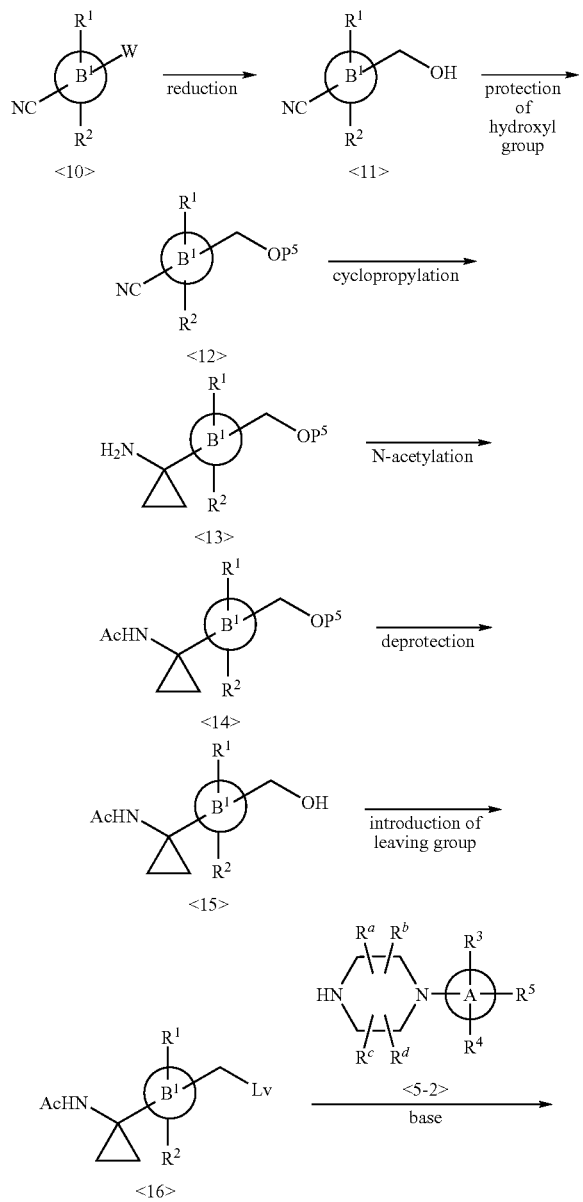

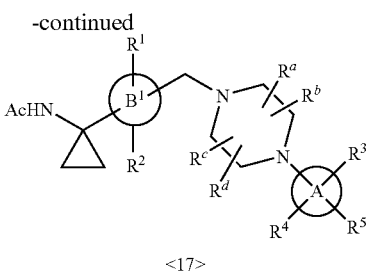

wherein W is a carboxylic acid derivative mutually easily convertible by a method basically and widely used in the field of organic synthetic chemistry, such as carboxylic acid and carboxylate, $P^5$ is a hydroxyl-protecting group widely used in the field of organic synthetic chemistry, such as tert-butyldimethylsilyl group and the like, and other symbols are as defined above.

Carboxylic acid derivative <10> is reduced by a method similar to Method L described in patent document 1 to give compound <11>, the hydroxyl group is protected with a suitable protecting group by the method described in, for example, non-patent document 10 and the like to give compound <12>, the cyano group is converted to a 1-aminocyclopropyl-1-yl group by the method described in J. Org. Chem. 2002, 67, 3965-3968, Organic Letters 2003, 5(5), 753-755 and the like to give compound <13>, the amino group is acetylated by the method described in, for example, non-patent document 10 or a method similar to Method B1 described in patent document 1 to give compound <14>, the hydroxyl-protecting group is removed by the method described in non-patent document 10 etc. to give compound <15>, and the hydroxyl group is converted to leaving group Lv by a method known in the field of organic synthetic chemistry, whereby compound <16> can be obtained. Examples of the method for converting hydroxyl group to leaving group Lv when the leaving group is a sulfonic acid ester such as methanesulfonyloxy and the like include a method including reacting alcohol <14> with alkyl or aryl chloride and the like in a nonaqueous solvent such as methylene chloride, tetrahydrofuran and the like, in the presence of a base such as triethylamine and the like. The reaction of compound <16> with compound <5-2> can be performed in the same manner as in Method A described in patent document 1.

Compounds other than compound <9> wherein m=n=0 in Y, $R^{12}$ and $R^{13}$ are groups that form ethylene in combination, one of $R^6$ and $R^7$ is hydrogen and the other is an acetyl group, and $R^8$ and $R^9$ are hydrogens, can be produced by combining a method similar to the above-mentioned and a known method.

As carboxylic acid derivative <10>, a commercially available product is used or can be synthesized from a commercially available halogenated allylcarboxylic acid derivative by, for example, the following Method A-b-1-1.

(Method A-b-1-1)

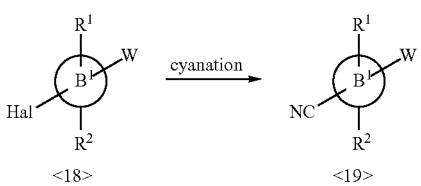

wherein Hal is halogen such as chlorine, bromine, iodine and the like, and other symbols are as defined above.

Compound <18> is cyanated to give <19>. Examples of the cyanation agent used for the cyanation reaction include sodium cyanide, potassium cyanide, copper cyanide, zinc cyanide, trimethylsilyl cyanide, p-toluenesulfonyl cyanide and the like. To promote the reaction, a combination of a metal salt such as palladium acetate and the like, and a ligand such as triphenylphosphine and the like, or a metal complex such as tetrakis(triphenylphosphine)palladium and the like, or a base such as N-methylpyrrolidine and the like may be used, or these may be used in combination. Examples of the solvent to be used for the cyanation reaction include lower alcohol such as methanol, ethanol and the like, acetonitrile, dimethylacetamide, dimethyl sulfoxide, N-methylpyrrolidone and the like and a mixture thereof. The reaction temperature is generally 0-150° C., and a temperature lower or higher than this range can be selected as necessary. The reaction time is generally within the range of 30 min to 2 days, and a time longer or shorter than this range can be selected as necessary.

The present invention can provide a therapeutic drug for cerebral infarction containing the above-mentioned compound as an active ingredient. The cerebral infarction includes atherothrombotic cerebral infarction, lacunar cerebral infarction and cardioembolic cerebral infarction.

Moreover, the present invention can provide a therapeutic drug for diseases involving inflammatory cytokines (TNF-α, IL-1β, IL-6, MCP-1, IL-8, IFN-γ etc.) relating to the brain spinal cord, which contains the above-mentioned compound as an active ingredient. Examples of the diseases involving inflammatory cytokines relating to the brain and spinal cord include infections such as encephalitis and encephalomyelitis, diseases caused by nerve inflammation of the central nervous system including autoimmune diseases and other diseases.

When the above-mentioned compounds are used as therapeutic drugs for cerebral infarction and the like, they are formulated as general pharmaceutical preparations. For example, the above-mentioned compound is mixed with a pharmaceutically acceptable carrier (excipient, binder, disintegrant, corrigent, flavor, emulsifier, diluent, solubilizer and the like) and formulated as a resulting pharmaceutical composition or in a form suitable for oral or parenteral preparation such as tablet, pill, powder, granule, capsule, troche, syrup, liquid, emulsion, suspension, injection (liquid, suspension etc.), suppository, inhalant, percutaneous absorber, eye drop, nasal drop, eye ointment and the like.

When a solid preparation is produced, additives such as sucrose, lactose, cellulose sugar, D-mannitol, maltitol, dextran, starches, agar, arginates, chitins, chitosans, pectins, trangacanths, gum arabics, gelatins, collagens, casein, albumin, calcium phosphate, sorbitol, glycine, carboxymethylcellulose, polyvinylpyrrolidone, hydroxypropylcellulose, hydroxypropylmethylcellulose, glycerol, polyethylene glycol, sodium hydrogen carbonate, magnesium stearate, talc and the like are used. Moreover, tablets can be processed into those having a general coating as necessary, for example, sugar-coated tablet, enteric tablet, film-coated tablet, two-layer tablet and multi-layer tablet.

When a semi-solid preparation is produced, animal and plant fats and oils (olive oil, corn oil, castor oil and the like), mineral oils (petrolatum, white petrolatum, solid paraffin and the like), waxes (jojoba oil, carnauba wax, beeswax and the like), partially synthesized or entirely synthesized glycerol acid esters (lauryl acid, myristic acid, palmitic acid and the like) and the like are used. Examples of commercially available products thereof include Witepsol (manufactured by Dynamid Novel), Pharmasol (manufactured by NOF Corporation) and the like.

When a liquid preparation is produced, additives such as sodium chloride, glucose, sorbitol, glycerol, olive oil, propylene glycol, ethyl alcohol and the like can be mentioned. Particularly, when an injection is produced, aseptic aqueous solutions, for example, saline, isotonic solution and oily liquids such as sesame oil and soybean oil are used. Where necessary, moreover, suitable suspending agents such as sodium carboxymethyl cellulose, non-ionic surfactants, solubilizers such as benzyl benzoate, benzyl alcohol and the like may be used in combination.

Moreover, when an eye drop or a nasal drop is produced, an aqueous liquid or aqueous solution is used and, particularly, an aseptic aqueous solution for injection can be mentioned. The liquid for eye drop or nasal drop may contain various additives as appropriate, such as buffers (borate buffer, acetate buffer, carbonate buffer and the like are preferable for reducing stimulation), isotonicity agent, solubilizer, preservative, thickener, chelating agent, pH adjuster (pH is preferably adjusted to generally about 6-8.5), aromatic and the like.

The amount of the active ingredient in these preparations is 0.1-100 wt %, suitably 1-50 wt %, of the preparation. While the dose varies depending on the symptom, body weight, age and the like of the patients, for oral administration, it is generally about 0.1-3000 mg per day for an adult, which is preferably administered in one to several portions.

EXAMPLES

The present invention is explained in more detail in the following by referring to Examples. However, the present invention is not limited to the following as long as it does not go beyond the gist thereof.

1. Compound Synthesis Example

Example 1

N-(1-{4-[(3,5-dimethyl-4-pyrimidin-2-ylpiperazin-1-yl)methyl]phenyl}cyclopropyl)acetamide

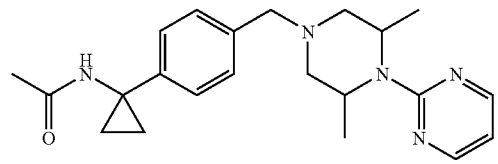 [SMILES: CC(=O)NC1(c2ccc(CN3CC(C)N(c4ncccn4)C(C)C3)cc2)CC1]

(1) Synthesis of 3,5-dimethylpiperazine-1-carboxylic acid tert-butyl ester

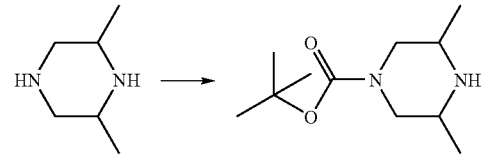

2,6-Dimethylpiperazine (5.71 g) was dissolved in dioxane (150 ml), di-tert-butyl bicarbonate (3.64 g) was added, and the mixture was stirred at room temperature overnight. The solvent was evaporated, water (50 ml) was added to the residue, and the mixture was extracted with dichloromethane (once with 100 ml and once with 50 ml). The extract was washed with saturated brine and dried over anhydrous sodium sulfate, and the solvent was evaporated to give the title compound (3.58 g).

$^1$H-NMR (CDCl$_3$) δ:1.06 (3H, d, J=6.3 Hz), 1.46 (9H, s), 2.23-2.31 (2H, m), 2.27-2.84 (2H, m), 3.80-4.15 (2H, m).

MS: 214 (M$^+$+1)

(2) Synthesis of 3,5-dimethyl-4-pyrimidin-2-ylpiperazine-1-carboxylic acid tert-butyl ester

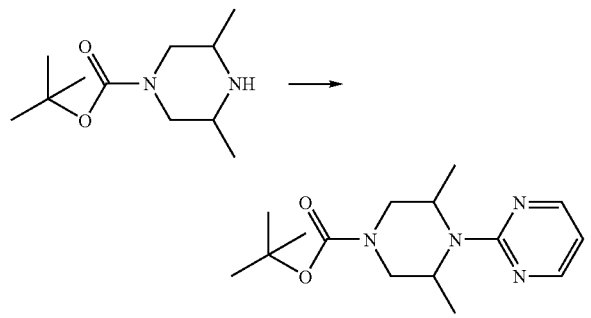

3,5-Dimethylpiperazine-1-carboxylic acid tert-butyl ester (1.676 g) and 2-chloropyrimidine (716 mg) were combined, melted in an oil bath at 120° C., and stirred for 5 hr 30 min. Water (10 ml) was added and the mixture was stirred, extracted with ethyl acetate (30 ml), and washed with saturated brine. The extract was dried over anhydrous sodium sulfate, and the solvent was evaporated. The obtained residue was purified by column chromatography (Yamazen HI-FLASH™ COLUMN size L, elution solvent: hexane/ethyl acetate) to give the title compound (333 mg).

$^1$H-NMR (CDCl$_3$) δ:1.25 (6H, d, J=6.9 Hz), 1.51 (9H, s), 2.97-3.08 (2H, m), 3.95-4.16 (2H, m), 4.65-4.82 (2H, m), 6.51 (1H, t, J=4.5 Hz), 8.34 (2H, d, J=4.8 Hz).

MS: 237 (M$^+$+1 when tert-butyl group was cleaved).

(3) Synthesis of 2-(2,6-dimethylpiperazin-1-yl)pyrimidine hydrochloride

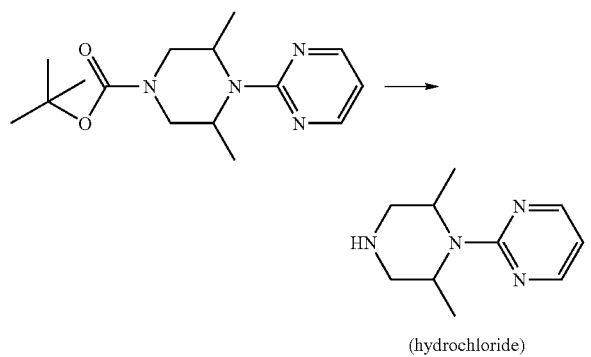

3,5-Dimethyl-4-pyrimidin-2-ylpiperazine-1-carboxylic acid tert-butyl ester (294 mg) was dissolved in ethanol (2 ml), 4N hydrochloric acid (ethyl acetate solution, 2 ml) was added and the mixture was stirred at room temperature for 4 hr. The solvent was evaporated, and ethyl acetate (3 ml) was added to the obtained residue. The solid insoluble in ethyl acetate was collected by filtration and dried to give the title compound (281 mg).

$^1$H-NMR (DMSO-d$_6$) δ:1.32 (6H, d, J=7.2 Hz), 3.12-3.43 (4H, m), 4.80-4.98 (2H, m), 6.74 (1H, t, J=5.1 Hz), 8.45 (2H, d, J=5.1 Hz), 9.26 (1H, brs), 10.02 (1H, brs).

MS: 193 (M$^+$+1)

(4) Synthesis of N-(1-{4-[(3,5-dimethyl-4-pyrimidin-2-ylpiperazin-1-yl)methyl]phenyl}cyclopropyl)acetamide

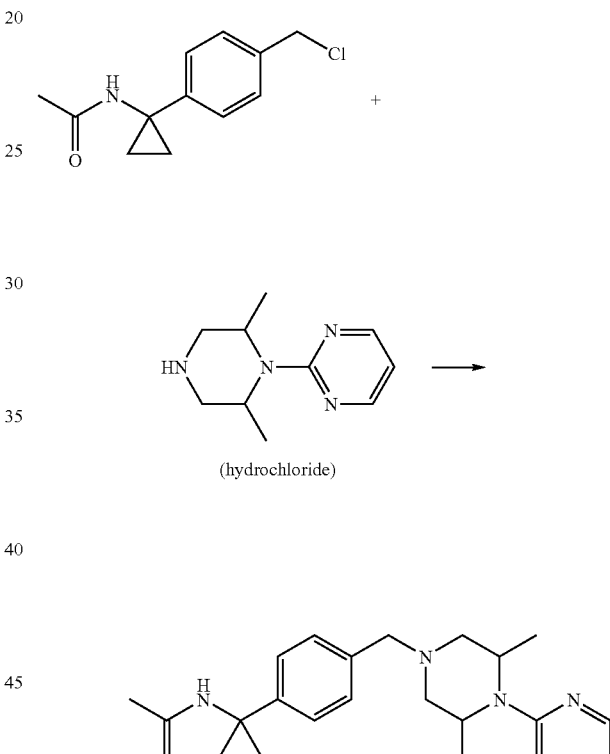

N-[1-(4-Chloromethylphenyl)cyclopropyl]acetamide (22.3 mg) and 2-(2,6-dimethylpiperazin-1-yl)pyrimidine hydrochloride (265 mg) were dissolved in N,N-dimethylformamide (10 mL), potassium carbonate (415 mg) was added and the mixture was stirred at 80° C. for 8 hr. Water (20 mL) was added and the mixture was stirred, extracted with ethyl acetate, and dried over anhydrous sodium sulfate. The solvent was evaporated and the obtained residue was purified by column chromatography (Yamazen HI-FLASH™ COLUMN size 2 L, elution solvent: hexane/ethyl acetate) to give the title compound (245 mg).

$^1$H-NMR (CDCl$_3$) δ:1.20-1.43 (10H, m), 2.01 (3H, s), 2.17-2.26 (2H, m), 2.74 (2H, d, J=11.1 Hz), 3.48 and 3.51 (2H, s and s), 4.63-4.69 (2H, m), 6.10 (1H, s), 6.43-6.47 (1H, m), 7.10-7.39 (4H, m), 8.32 (1H, d, J=4.8 Hz)

MS: 380 (M$^+$+1)

Example 2

N-[1-(4-{[(3S)-3-methyl-4-pyrimidin-2-ylpiperazin-1-yl]methyl}phenyl)cyclopropyl]acetamide

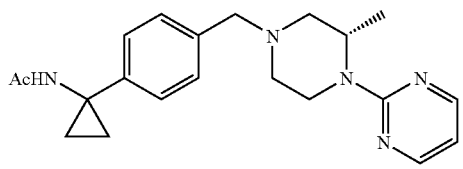 [SMILES: CC(=O)NC1(c2ccc(CN3CCN(c4ncccn4)[C@@H](C)C3)cc2)CC1]

Using (3S)-1-tert-butyloxycarbonyl-3-methylpiperazine, reactions similar to those in Example 1 (2), (3) were successively performed to give (3S)-3-methyl-4-pyrimidin-2-ylpiperazine hydrochloride, then reactions similar to those in Example 1 (4) were successively performed to give the title compound (216 mg).

$^1$H-NMR (CDCl$_3$) δ:1.27-1.38 (7H, d and m, J=6.3 Hz), 2.01 (3H, s), 2.07-2.21 (2H, m), 2.71 (2H, d, J=11.1 Hz), 2.89 (1H, d, J=10.8 Hz), 3.16-3.26 (1H, m), 3.39 (1H, d, J=13.2 Hz), 3.54 (1H, d, J=13.2 Hz), 4.44 (1H, d, J=12.9 Hz), 4.81 (1H, brs), 6.69 (1H, s), 6.43-6.47 (1H, m), 7.09-7.34 (4H, m), 8.30 (1H, d, J=4.8 Hz)

MS: 366 (M$^+$+1)

Example 3

N-[1-(4-{[(1S,4S)-5-(pyrimidin-2-yl)-2,5-diazabicyclo[2.2.1]hept-2-yl]methyl}phenyl)cyclopropyl]acetamide

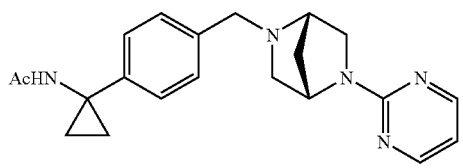 [SMILES: CC(=O)NC1(c2ccc(CN3C[C@@H]4C[C@H]3CN4c3ncccn3)cc2)CC1]

Using (1S,4S)-2,5-diazabicyclo[2.2.1]heptane, reactions similar to those in Example 1 (2), (3) were successively performed to give (1S,4S)-2-pyrimidin-2-yl-2,5-diazabicyclo[2.2.1]heptane hydrochloride, then reactions similar to those in Example 1 (4) were performed to give the title compound (201 mg).

$^1$H-NMR (DMSO-d$_6$) δ: 1.09 (4H, d, J=2.7 Hz), 1.75 (1H, d, J=9.6 Hz), 1.88 (3H, s), 1.90 (1H, d, J=9.6 Hz), 2.44 (1H, d, J=9.6 Hz), 2.83 (1H, dd, J=2.1 Hz, 9.6 Hz), 3.56 (1H, d, J=18.6 Hz), 3.63 (2H, s), 4.71 (1H, s), 6.58 (1H, t, J=5.1 Hz), 7.04 (2H, d, J=8.4 Hz), 7.19 (2H, d, J=8.4 Hz), 8.31 (2H, d, J=4.8 Hz), 8.51 (1H, s).

MS: 364 (M$^+$+1)

Example 4

N-(1-{4-[{2,5-dimethyl-4-(pyrimidin-2-yl)}piperazin-1-yl)methyl]phenyl}cyclopropyl)acetamide

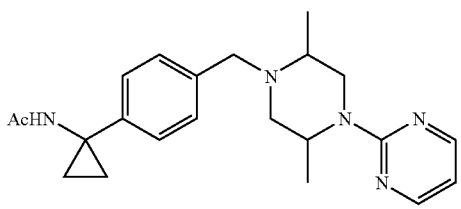 [SMILES: CC(=O)NC1(c2ccc(CN3CC(C)N(c4ncccn4)CC3C)cc2)CC1]

Using 2,5-trans-dimethylpiperazine, reactions similar to those in Example 1 (1), (2), (3) were successively performed to give 2-(2,5-dimethylpiperazin-1-yl)pyrimidine hydrochloride, then reactions similar to those in Example 1 (4) were performed to give the title compound (64 mg).

$^1$H-NMR (DMSO-d$_6$) δ:0.91 (3H, d, J=6.6 Hz), 1.12 (4H, d, J=5.4 Hz), 1.18 (3H, d, J=6.6 Hz), 1.84 (3 Hs), 2.29 (1H, d, J=11.4 Hz), 2.69 (1H, dd, J=4.5 Hz, 12.0 Hz), 3.02 (1H, m), 3.44 (1H, d, J=13.5 Hz), 3.59 (1H, d, J=13.4 Hz), 4.33 (1H, d, J=13.5 Hz), 4.75 (1H, t, J=5.1 Hz), 6.57 (1H, t, J=4.5 Hz), 7.07 (2H, d, J=8.1 Hz), 7.26 (2H, d, J=8.1 Hz), 8.32 (2H, d, J=5.1 Hz), 8.52 (1H, s).

MS: 380 (M$^+$+1)

Example 5

N-[1-(4-{[((2R)-2-methyl-4-(pyrimidin-2-yl))piperazin-1-yl]methyl}phenyl)cyclopropyl]acetamide

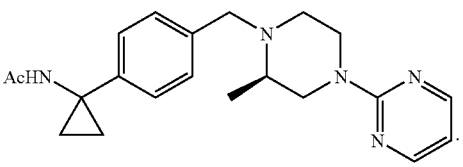 [SMILES: CC(=O)NC1(c2ccc(CN3CCN(c4ncccn4)C[C@H]3C)cc2)CC1]

(1) Synthesis of (3R)-4-{4-[1-(acetylamino)cyclopropyl]benzyl}-3-methylpiperazine-1-carboxylic acid tert-butyl ester

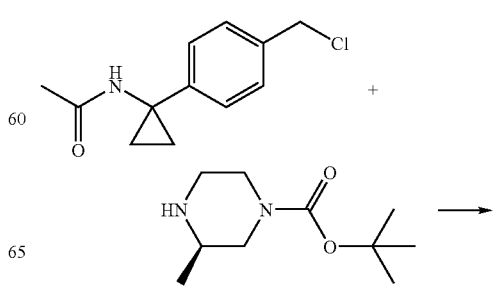

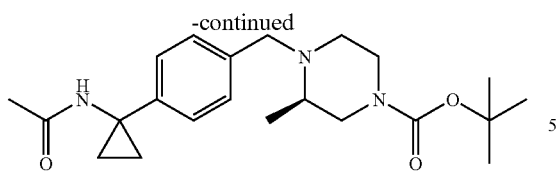

Reaction and treatment in the same manner as in Example 1 (4) and using (3R)-1-tert-butyloxycarbonyl-3-methylpiperazine (1.00 g) instead of 2-(2,6-dimethylpiperazin-1-yl)pyrimidine hydrochloride were performed to give the title compound (1.119 g).

$^1$H-NMR (DMSO-$d_6$) δ:1.03 (3H, d, J=6.3 Hz), 1.10 (4H, m), 1.38 (9H, s), 1.83 (3H, s), 2.00 (1H, n), 2.36 (1H, m), 2.54 (1H, m), 2.89 (1H, m), 3.02 (1H, m), 3.15 (1H, d, J=13.2 Hz), 3.42-3.55 (2H, m), 3.83 (1H, d, J=13.2 Hz), 7.05 (2H, d, J=8.1 Hz), 7.17 (2H, d, J=8.1 Hz), 8.52 (1H, s).

MS: 388 (M$^+$+1).

(2) Synthesis of N-[1-4-{[(2R)-methylpiperazin-1-yl]methyl}phenyl]cyclopropyl]acetamide hydrochloride

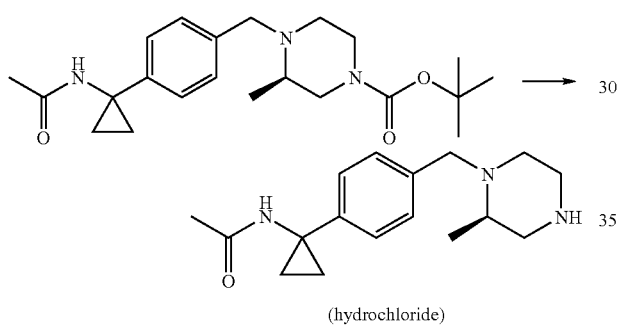

(hydrochloride)

(3R)-4-4{4-[1-(Acetylamino)cyclopropyl]benzyl}-3-methylpiperazine-1-carboxylic acid tert-butyl ester (1.097 g) was dissolved in ethanol (2 ml), 4N hydrochloric acid (ethyl acetate solution, 2 ml) was added thereto, and the mixture was stirred at room temperature for 4 hr. The solvent was evaporated to give the title compound (1.11 g).

$^1$H-NMR (DMSO-$d_6$) δ:1.17 (4H, m), 1.57 (3H, d, 5.7 Hz), 1.87 (3H, s), 3.00-3.60 (7H, m), 4.16 (1H, d, J=12.9 Hz), 4.64 (1H, d, J=12.9 Hz), 7.16 (2H, d, J=7.8 Hz), 7.52 (2H, d, J=7.8 Hz), 8.64 (1H, s), 9.84 (2H, brs), 12.33 (1H, brs).

MS: 288 (M$^+$+1)

(3) Synthesis of N-[1-(4-{[((2R)-2-methyl-4-(pyrimidin-2-yl))piperazin-1-yl]methyl}phenyl)cyclopropyl]acetamide

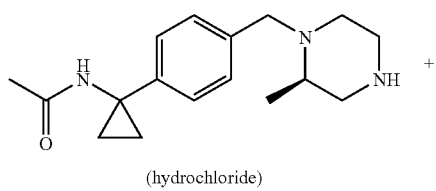

(hydrochloride)

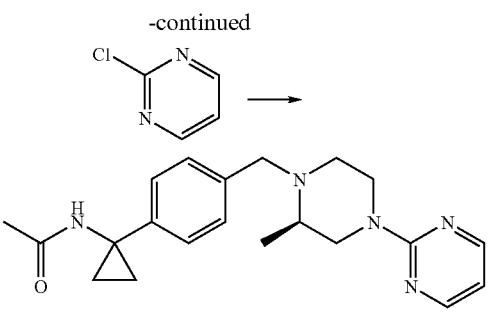

N-[1-4-{[(2R)-Methylpiperazin-1-yl]methyl}phenyl]cyclopropyl]acetamide hydrochloride (532 mg), 2-chloropyrimidine (170 mg) and diisopropylethylamine (0.75 ml) were heated in an oil bath at 100° C. for 2 hr 10 min. Water (20 ml) was added, and the mixture was extracted with toluene (20 ml, twice) and ethyl acetate (30 ml, once), and the organic layer was washed successively with water and saturated brine. The organic layer was dried over anhydrous sodium sulfate, the solvent was evaporated, and the obtained residue was purified by column chromatography (Yamazen HI-FLASH™ COLUMN size L, elution solvent: hexane/ethyl acetate) to give the title compound (196 mg).

$^1$H-NMR (DMSO-$d_6$) δ:1.05-1.12 (7H, m), 1.84 (1H, s), 2.06 (1H, m), 2.43 (1H, m), 2.62 (1H, m), 3.05 (1H, dd, J=8.7 Hz, 12.9 Hz), 3.13 (1H, d, J=13.2 Hz), 3.20 (1H, m), 3.92 (1H, d, J=13.2 Hz), 4.14 (1H, m), 4.19 (1H, m), 6.59 (1H, t, J=4.8 Hz), 7.07 (2H, d, J=8.4 Hz), 7.21 (2H, d, J=8.4 Hz), 8.32 (2H, d, J=4.8 Hz), 8.52 (1H, s).

MS: 366 (M$^+$+1)

Example 6

N-(1-{4-[{(2,6-dimethyl-4-(pyrimidin-2-yl))piperazin-1-yl}methyl]phenyl}cyclopropyl)acetamide

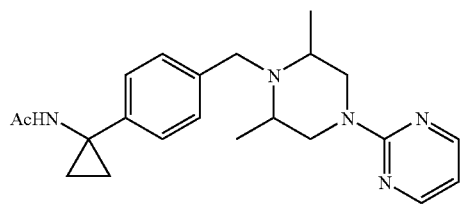 [SMILES: CC(=O)NC1(c2ccc(CN3C(C)CN(c4ncccn4)CC3C)cc2)CC1]

Using 3,5-dimethylpiperazine-1-carboxylic acid tert-butyl ester (1.676 g) synthesized in Example 1 (1) and in the same manner as in Example 5 (1), 4-{4-[1-(acetylamino)cyclopropyl]benzyl}-3,5-dimethylpiperazine-1-carboxylic acid tert-butyl ester (333 mg) was synthesized, and reactions similar to those in Example 5 (2), (3) were successively performed to give the title compound (230 mg).

$^1$H-NMR (DMSO-$d_6$) δ: 1.01 (6H, d, J=6.0 Hz), 1.09 (4H, d, J=4.5 Hz), 1.83 (3H, s), 2.74 (2H, dd, J=10.5 Hz, 12.6 Hz), 3.28 (2H, d, J=12.9 Hz), 3.72 (2H, s), 4.41 (2H, d, J=11.4 Hz), 6.59 (1H, t, J=4.5 Hz), 7.04 (2H, d, J=7.8 Hz), 7.25 (2H, d, J=7.8 Hz), 8.33 (2H, d, J=4.5 Hz), 8.50 (1H, s).

MS: 380 (M$^+$+1)

Example 7

N-(1-{5-[{4-(pyrimidin-2-yl)piperazin-1-yl}methyl]pyridin-2-yl}cyclopropyl)acetamide

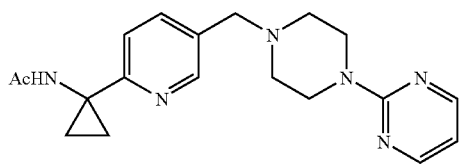 [SMILES: CC(=O)NC1(c2ccc(CN3CCN(c4ncccn4)CC3)cn2)CC1]

(1) Synthesis of 6-cyanonicotinic acid methyl ester

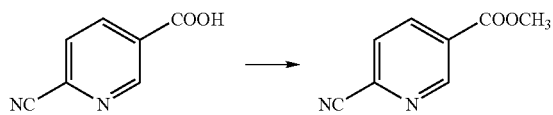

6-Cyanonicotinic acid (500 mg) was dissolved in dichloromethane (25 ml), water-soluble carbodiimide (776 mg), methanol (0.164 ml) and 4-dimethylaminopyridine (49 mg) were added thereto, and the mixture was stirred for 2 hr 10 min. The reaction mixture was washed successively with saturated aqueous sodium hydrogen carbonate and saturated brine and dried over anhydrous sodium sulfate. The solvent was evaporated, and the obtained residue was purified by column chromatography (Yamazen HI-FLASH™ COLUMN size 2 L, elution solvent: hexane/ethyl acetate) to give the title compound. The same reactions were repeated using 6-cyanonicotinic acid (547 mg) to give the title compound (total 951 mg).

$^{1}$H-NMR (CDCl$_{3}$) δ:4.01 (3H, s), 7.81 (1H, dd, J=1.2 Hz, 8.1 Hz), 8.45 (1H, dd, J=2.4 Hz, 8.1 Hz), 9.30 (1H, t, J=1.2 Hz).

MS: 163 (M$^{+}$+1)

(2) Synthesis of 5-(hydroxymethyl)pyridine-2-carbonitrile

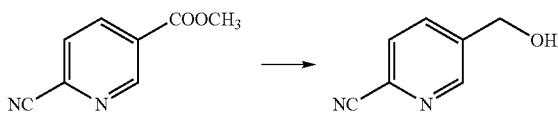

6-Cyanonicotinic acid methyl ester (701 mg) was dissolved in a mixed solvent of methanol (1 ml) and tetrahydrofuran (7 ml) and sodium borohydride (197 mg) was added under ice-cooling. The mixture was directly heated to room temperature and stirred overnight. Water (20 ml) was added, and the mixture was extracted with ethyl acetate (once with 50 ml and once with 30 ml), washed with saturated brine, and dried over anhydrous sodium sulfate. The solvent was evaporated and the obtained residue was purified with column chromatography (Yamazen HI-FLASH™ COLUMN size 2 L, elution solvent: hexane/ethyl acetate) to give the title compound (264 mg).

$^{1}$H-NMR (CDCl$_{3}$) δ:2.09 (1H, m), 4.86 (2H, d, J=5.1 Hz), 7.71 (1H, d, J=8.1 Hz), 7.89 (1H, dd, J=1.8 Hz, 8.1 Hz), 8.70 (1H, s).

MS: 135 (M$^{+}$+1).

(3) Synthesis of 5-(tert-butyldimethylsilanyloxymethyl)-pyridine-2-carbonitrile

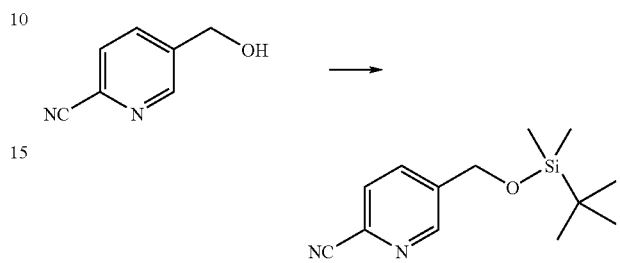

5-(Hydroxymethyl)pyridine-2-carbonitrile (258 mg) was dissolved in dimethylformamide (8 ml), tert-butyl dimethylchlorosilane (347 mg) and imidazole (326 mg) were added, and the mixture was stirred at room temperature for 1½ hr. Water (20 ml) was added and the mixture was stirred, extracted with ethyl acetate (once with 50 ml and once with 20 ml), washed with saturated brine, and dried over anhydrous sodium sulfate. The solvent was evaporated and the obtained residue was purified by column chromatography (Yamazen HI-FLASH™ COLUMN size 2 L, elution solvent: hexane/ethyl acetate) to give the title compound (405 mg).

$^{1}$H-NMR (CDCl$_{3}$) δ:0.13 (6H, s), 0.95 (9H, s), 4.83 (2H, s), 7.68 (1H, d, J=7.8 Hz), 7.81 (1H, dd, J=1.5 Hz, 7.8 Hz), 8.66 (1H, d, J=1.5 Hz).

MS: 249 (M$^{+}$+1).

(4) Synthesis of 1-[5-(tert-butyldimethylsilanyloxymethyl)pyridin-2-yl]cyclopropylamine

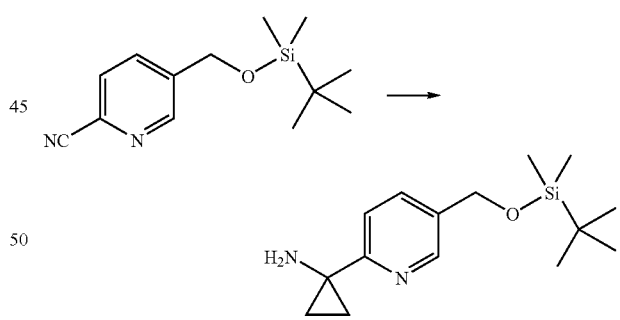

5-(tert-Butyldimethylsilanyloxymethyl)-pyridine-2-carbonitrile was dissolved in tetrahydrofuran (10 ml), titanium tetraisopropoxide (0.62 ml) was added thereto, and a solution of ethylmagnesium bromide in tetrahydrofuran (1 mol/l, 4.83 ml) was added dropwise. The mixture was stirred for 1 hr 30 min. To the reaction mixture was added 1N aqueous sodium hydroxide solution (6 ml) and tetrahydrofuran (20 ml) was further added, and the mixture was stirred and filtered. The filtrate was washed with saturated brine and dried over anhydrous sodium sulfate, and the solvent was evaporated. The obtained residue was purified by column chromatography (Yamazen HI-FLASH™ COLUMN size 2 L, elution solvent: hexane/ethyl acetate) to give the title compound (192 mg).

¹H-NMR (CDCl₃) δ:0.10 (6H, s), 0.93 (9H, s), 1.13 (2H, m), 1.26 (2H, m), 4.72 (2H, s), 7.31 (2H, d, J=8.1 Hz), 7.58 (2H, d, J=2.1 Hz, 8.1 Hz), 8.44 (1H, s).
MS: 280 (M⁺+1).

(5) Synthesis of 1-[5-(tert-butyldimethylsilanyloxymethyl)pyridin-2-yl]cyclopropylacetamide

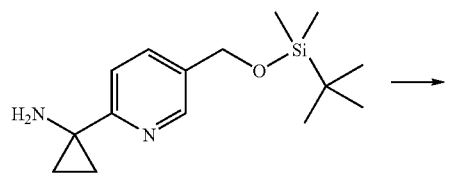

1-[5-(tert-Butyldimethylsilanyloxymethyl)pyridin-2-yl]cyclopropylamine (190 mg) was dissolved in pyridine (2 ml), acetic anhydride (0.13 ml) and 4-dimethylaminopyridine (17 mg) were added, and the mixture was stirred at room temperature for 4 hr. Methanol (2 ml) was added and the mixture was stirred for about 10 min. The solvent was evaporated, and the residue was purified by column chromatography (Yamazen HI-FLASH™ COLUMN size L, elution solvent: hexane/ethyl acetate) to give the title compound (158 mg).
¹H-NMR (CDCl₃) δ:0.09 and 0.11 (6H, s), 0.92 and 0.94 (9H, s), 1.24-1.32 (2H, m), 1.60-1.76 (2H, m), 1.99, 2.07 (3H, s), 4.73 and 4.76 (2H, s), 6.12 and 6.24 (1H, s), 7.29 and 7.44 (2H, d, J=8.1 Hz), 7.56 and 7.61 (2H, dd, J=1.8 Hz, 8.1 Hz), 8.40 and 8.44 (1H, d, J=1.5 Hz).
MS: 321 (M⁺+1).

(6) Synthesis of N-{1-[5-(hydroxymethyl)pyridin-2-yl]cyclopropyl}acetamide

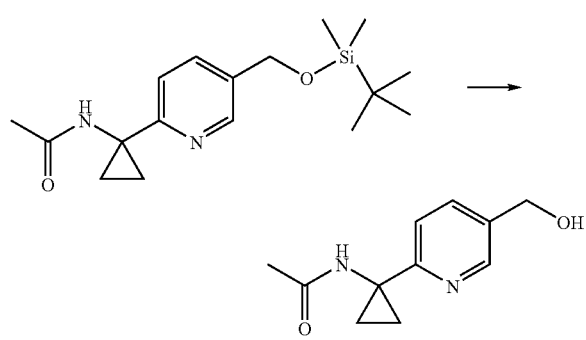

1-[5-(tert-Butyldimethylsilanyloxymethyl)pyridin-2-yl]cyclopropylacetamide (156 mg) was dissolved in tetrahydrofuran (2 ml), and a solution (1 mol/l, 1.46 ml) of tetrabutylammonium fluoride in tetrahydrofuran was added thereto. The mixture was stirred at room temperature for 25 min. The solvent was evaporated and the obtained residue was purified by column chromatography (Yamazen HI-FLASH™ COLUMN size L, elution solvent: ethyl acetate/methanol) to give the title compound (109 mg).

¹H-NMR (DMSO-d₆) δ:1.07 (2H, m), 1.40 (2H, m), 1.90 (3H, s), 4.46 (2H, d, J=5.7 Hz), 5.22 (1H, t, J=5.7 Hz), 7.28 (2H, d, J=8.1 Hz), 7.60 (2H, dd, J=2.1 Hz, 8.1 Hz), 8.33 (1H, d, J=1.8 Hz), 8.62 (1H, s).
MS: 207 (M⁺+1).

(7) Synthesis of N-(1-{5-[{4-(pyrimidin-2-yl)piperazin-1-yl}methyl]pyridin-2-yl}cyclopropyl)acetamide

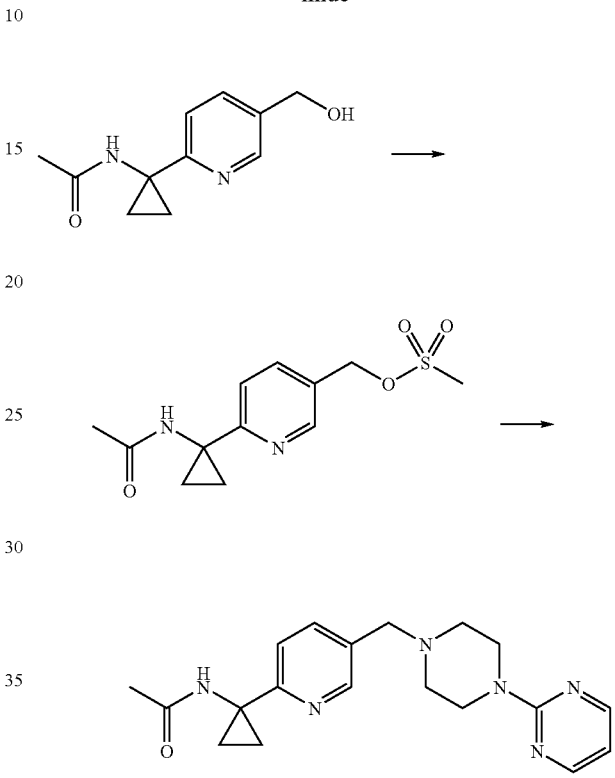

N-{1-[5-(Hydroxymethyl)pyridin-2-yl]cyclopropyl}acetamide (100 mg) was dissolved in tetrahydrofuran (10 ml), methanesulfonyl chloride (0.045 ml) and triethylamine (0.080 ml) were added thereto and the mixture was stirred for 2 hr 50 min. Water (10 ml) was added thereto and the mixture was stirred. The mixture was extracted with ethyl acetate (20 ml, twice), washed successively with saturated aqueous sodium hydrogen carbonate solution and saturated brine, and dried over anhydrous sodium sulfate. The solvent was evaporated and the obtained residue was dissolved in dimethylformamide (2 ml). Potassium carbonate (134 mg) and 1-(2-pyrimidyl)piperazine (120 mg) were added, and the mixture was heated in an oil bath at 80° C. for 1 hr. Water (10 ml) was added thereto and the mixture was stirred, extracted with ethyl acetate (once with 30 ml and twice with 20 ml), washed with saturated brine, and dried over anhydrous sodium sulfate. The solvent was evaporated and the obtained residue was purified by column chromatography (Yamazen HI-FLASH™ COLUMN size L, elution solvent: ethyl acetate/methanol) to give the title compound (63.9 mg).
¹H-NMR (DMSO-d₆) δ:1.08 (2H, dd, J=4.1 Hz, 7.2 Hz), 1.42 (2H, dd, J=4.1 Hz, 7.2 Hz), 1.90 (3H, s), 2.40 (4H, t, J=4.7 Hz), 3.48 (2H, s), 3.70 (4H, t, H=4.7 Hz), 6.61 (1H, t, J=4.6 Hz), 7.29 (1H, d, J=8.0 Hz), 7.63 (1H, dd, J=2.1 Hz, 8.2 Hz), 8.34 (3H, m), 8.63 (1H, s).
MS: 353 (M⁺+1).

Example 8

N-[1-(5-{[(1S,4S)-5-(pyrimidin-2-yl)-2,5-diazabicyclo[2.2.1]hept-2-yl]methyl}pyridin-2-yl)cyclopropyl]acetamide

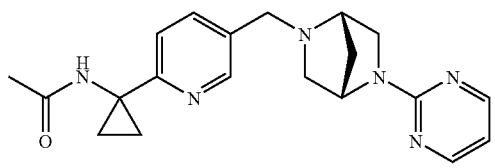 [SMILES: CC(=O)NC1(c2ccc(CN3C[C@@H]4C[C@H]3CN4c3ncccn3)cn2)CC1]

N-{1-[5-(Hydroxymethyl)pyridin-2-yl]cyclopropyl}acetamide (3.13 g) was dissolved in tetrahydrofuran (150 ml), methanesulfonyl chloride (1.76 ml) and triethylamine (4.25 ml) were added thereto and the mixture was stirred for 1 hr. Water (150 ml) was added thereto and the mixture was stirred, extracted with ethyl acetate, and dried over anhydrous sodium sulfate. The solvent was evaporated and diisopropyl ether was added to the obtained residue to give 3.76 g of a white solid. The white solid (1.16 g) and (1S,4S)-2-pyrimidin-2-yl-2,5-diazabicyclo[2.2.1]heptane hydrochloride (2.02 g) were dissolved in dimethylformamide (25 ml), potassium iodide (679 mg) and potassium carbonate (3.84 g) were added thereto and the mixture was heated in an oil bath at 80° C. for 1.5 hr. The reaction mixture was cooled to room temperature and ethyl acetate was added thereto. The precipitated solid was filtered off and concentrated under reduced pressure and the obtained residue was purified by column chromatography (silica gel BW-300, elution solvent: chloroform/methanol) to give the title compound (1.05 g).

$^1$H-NMR (DMSO-$d_6$) δ:0.95-1.14 (m, 2H), 1.32-1.55 (m, 2H), 1.70-1.82 (m, 1H), 1.89 (3H, s), 1.89-1.94 (m, 1H), 2.46 (1H, d, J=9.4 Hz), 2.84 (1H, J=9.5, 0.9, 0.8H, ddd), 3.48 (2H, s), 3.28-3.35 (m, 1H), 3.55 (1H, brs), 3.60 (1H, dd, J=10.3, 0.9H), 3.66 (Brs, 2H), 4.72 (1H, s), 6.59 (1H, t, J=4.8 Hz), 7.25 (1H, d, J=8.2 Hz), 7.61 (1H, dd, J=7.9 Hz, 2.1 Hz), 8.34 (3H, m), 8.19-8.45 (m, 3H), 8.61 (1H, s).

MS: 365 (M$^+$+1).

2. Effect on Cerebral Infarction Model

Test compound A used below was produced according to the method described in patent document 1, Example 71.

test compound A: N-(1-(4-((4-(pyrimidin-2-yl)piperazin-1-yl)methyl)phenyl)cyclopropyl)acetamide•hydrochloride

Pharmacological Experimental Example 1

Action on Intracerebral Production of TNF-α, IL-1β, IL-6 and MCP-1 in Rat Middle Cerebral Artery Occlusion-Reperfusion Model The middle cerebral artery of male Wistar rats (Japan Laboratory animals Inc.) was obstructed with suture (silicon-coated nylon thread), and test compound A (10 mg/kg) dissolved in saline was intravenously administered in 30 min after occlusion, and middle cerebral artery was reperfused in 60 min after administration. In only the rats used for TNF-α measurement, test compound A was administered orally. The brain was isolated at 12 hr after the occlusion (see Koizumi, J. et al., Jpn. J. Stroke, 8, 1-8, 1986). The brain tissue was homogenized, the centrifuged supernatant was collected and cytokine and chemokine were measured by ELISA. Intracerebral TNF-α, IL-1β and IL-6 were measured using an Immunoassay Kit (BIOSOURCE) according to the manufactures' protocol. MCP-1 was measured using an MCP-1 Instant ELISA (Bener MedSystems) according to the manufactures' protocol.

As a result, the concentration of TNF-α, IL-1μ and IL-6, which are intracerebral inflammatory cytokines, and MCP-1, which is chemokine, increased by transient cerebral ischemia [FIG. 1-4]. The test compound A suppressed each of the increased concentrations of TNF-α, IL-1β, IL-6 and MCP-1.

Pharmacological Experimental Example 2

Action on Brain Injury Volume and Neurological Deficit in Monkey Middle Cerebral Artery Permanent Occlusion Model In monkey middle cerebral artery permanent occlusion model, the brain injury volume was measured by MR[1] (FLAIR method) one day and seven days after occlusion. Test compound A (5 mg/kg) dissolved in 0.5% tragacanth was repeatedly administered orally twice a day for 14 days. As for neurological score, the neurological function was evaluated by scoring the consciousness, perception, motility and muscular commands.

The middle cerebral artery permanent occlusion was conducted according to the method of Furuichi et al. (Furuichi, Y et al., J. Cereb. Blood Flow Metab., 23, 1183-1194, 2003), which is specifically as follows. *Macaca fascicularis* fasted in advance for 12 hr or longer was anesthetized by intramuscular administration of ketamine hydrochloride (10 mg/kg), anesthetized by intravenous administration of pentobarbital sodium (25 mg/kg) and fixed on an operating table. About 5 mm holes were made near foramen ovale and orbital fissure with a dental drill, dura mater and arachnoid mater were incised, and the middle cerebral artery trunk near the internal carotid artery bifurcation area was exposed. The middle cerebral artery trunk near the internal carotid artery bifurcation area was obstructed by electric coagulation to form cerebral infarction.

Test compound A was orally administered within 1 hr and 6 hr after middle cerebral artery occlusion and within 30 min after feeding in the morning and evening (twice a day) from the next day for 14 days.

Figure 5:
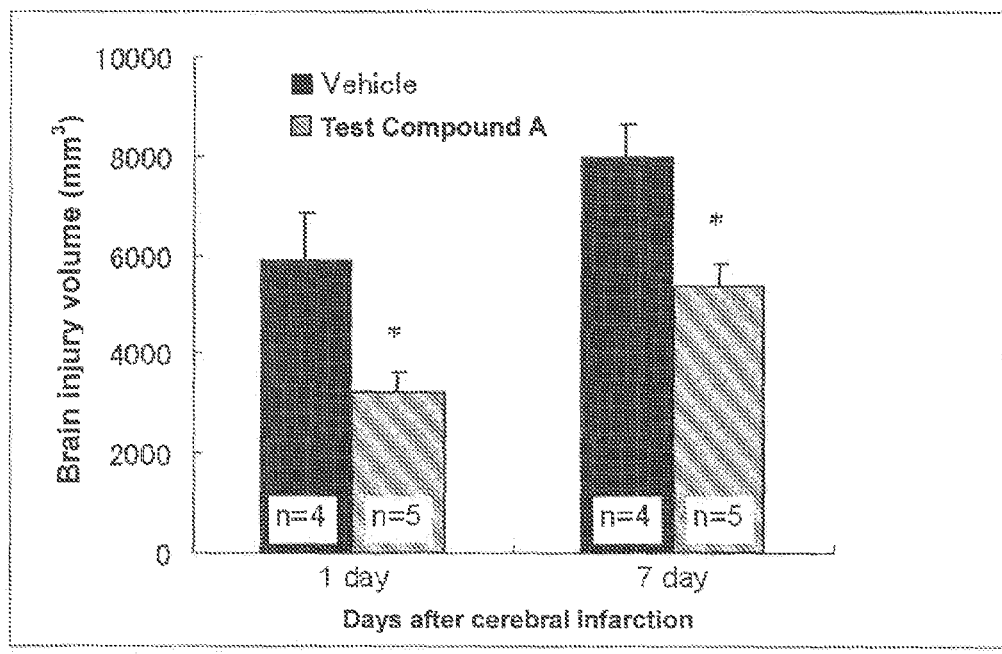
FIG. 5 shows brain injury volume of monkey middle cerebral artery permanent occlusion model, wherein a black column shows a Vehicle group (0.5% tragacanth alone administration group), and a hatched column shows a test compound A administration group.
Figure 6:
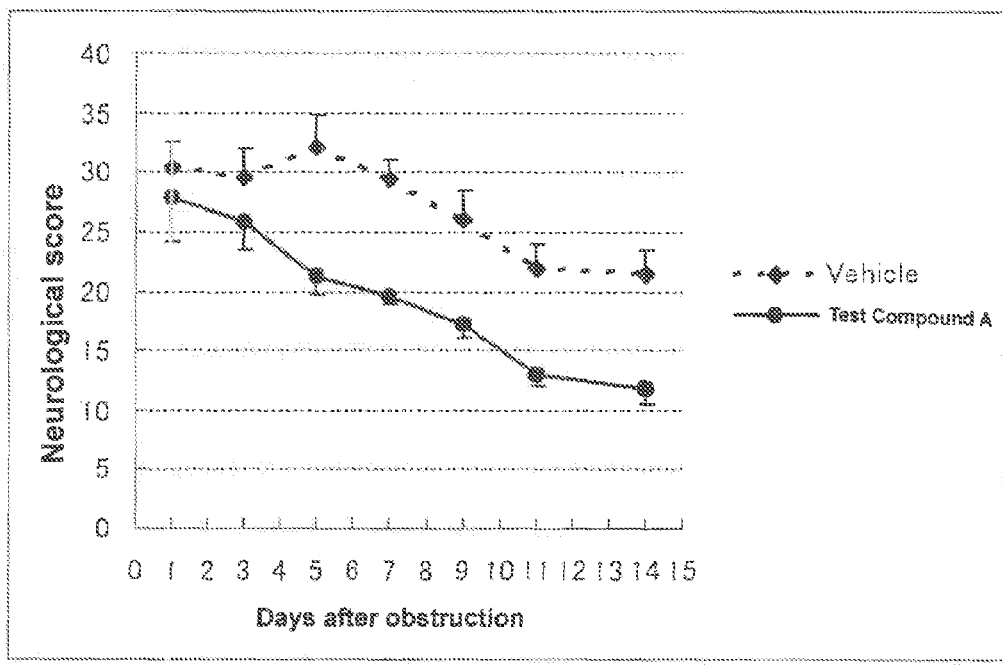
FIG. 6 shows scores of neurological function in monkey middle cerebral artery permanent occlusion model, wherein a dotted line graph is a Vehicle group (0.5% tragacanth alone administration group) and a solid line graph is a test compound A administration group.

In 7 cases for each group, 3 cases from the vehicle group and 2 cases from the test compound A group died. Excluding the death cases, the results reveal that test compound A showed a suppressive action on the spread of the cerebral infarction region both at 1 day and 7 days after middle cerebral artery occlusion [FIG. 5]. In addition, test compound A showed a neurological deficit-ameliorating effect [FIG. 6].

Pharmacological Experimental Example 3

Action on Intracerebral Cytokine Production in Mouse

LPS (lipopolysaccharide, derived from *E. coli* 0111:B4, Sigma, 500 μg/kg) was intraperitoneally administered to male BALB/c mouse (Charles River Laboratories Japan). After 90 min after LPS administration, the blood was taken under anesthesia, and centrifuged to collect plasma. TNF-α was measured using an Immunoassay Kit (R&D Systems) and IL-10, MCP-1 and IL-6 were measured using an Immunoassay Kit (BIOSOURCE). Test compound A, the compound synthesized in Example 3 (test compound B) and the compound synthesized in Example 7 (test compound C) were dissolved in saline, and the mixture was orally administered at 10 mg/kg 30 min before LPS administration. The results are shown in Tables 1, 2 and 3. As shown in the Tables, the effect of each test compound on respective intracerebral cytokines was calculated as the ratio of each cytokine concentration in the blood of the group administered with each test compound to each cytokine concentration in the blood of the group free of administration of each test compound.

Respective test compounds A, B and C suppressed TNF-α, IL-6 and MCP-1 production in the above-mentioned LPS model mouse and increased IL-10.

TABLE 1

| Test compound | TNF-α production (%) | IL-10 production (%) |
|---|---|---|
| A | 43.5 | 397.1 |
| B | 53.9 | 350.1 |
| C | 50.6 | 401.4 |

TABLE 2

| Test compound | IL-6 production (%) | MCP-1 production (%) |
|---|---|---|
| A | 74.4 | 61.7 |
| B | 78.7 | 63.9 |

TABLE 3

| Test compound | IL-6 production (%) | MCP-1 production (%) |
|---|---|---|
| A | 78.4 | 72.2 |
| C | 81 | 72.1 |

Pharmacological Experimental Example 4

Action on Cerebral Infarction Volume in Rat Middle Cerebral Artery Occlusion-Reperfusion Model The middle cerebral artery of male Wistar rats (Japan Laboratory Animals Inc.) was obstructed with suture (silicon-coated nylon thread), and saline (Vehicle, n=7), test compound A (10 mg/kg, n=6) dissolved in saline, test compound B (10% mg/kg, n=7) dissolved in saline, and test compound C (10 mg/kg, n=7) dissolved in saline were each intravenously administered in 30 min after occlusion and the artery was reperfused in 90 min after occlusion. The brain was isolated 24 hr later. A 2 mm brain strip was prepared, and the strip was stained with PBS (pH 7.4, 37° C.) containing 1% 2,3,5-triphenyltetrazolium chloride (TTC, Wako Pure Chemical Industries, Ltd.). The cerebral infarction area was measured by image analysis and the cerebral infarction volume was calculated.

Figure 7:
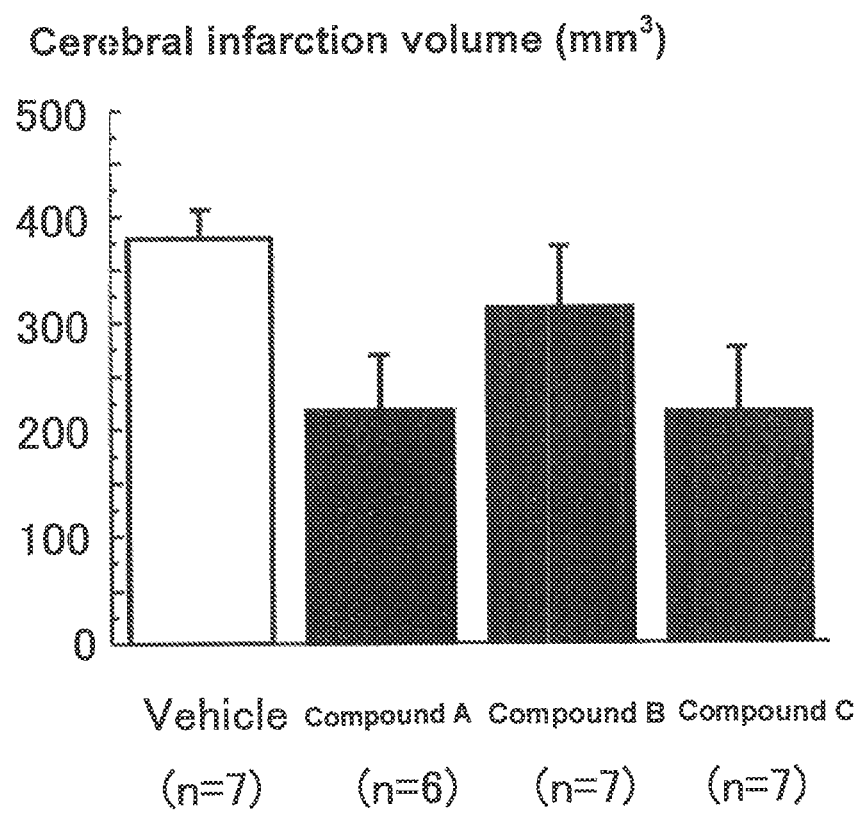
FIG. 7 shows cerebral infarction volume of rat middle cerebral artery occlusion-reperfusion model, wherein a white column is a Vehicle group (saline alone administration group) and a black column is a test compound administration group.

As a result, compound A, compound B and compound C suppressed cerebral infarction volume by 42.5%, 17.8% and 43.2%, respectively [FIG. 7].

Pharmacological Experimental Example 5

Evaluation of Bioavailability in Rat

Test compound A, test compound B and test compound C were each dissolved in 0.5% aqueous HPMC (hydroxypropyl methylcellulose) solution in the case of oral administration, or in saline in the case of intravenous administration, and they were orally or intravenously administered to male SD(IGS) rats (Charles River Laboratories Japan) by 3 mg/kg. The concentration of unchanged drug in the plasma of each rat was measured, and bioavailability (F(%)) was calculated (F (%)=(AUC$_{0-\infty,p.o.}$/AUC$_{0-\infty,i.v.,mean}$)×(Dose$_{i.v.}$/Dose$_{p.o.}$)× 100). The test compound was administered by gavage using an oral gavage needle (p.o.), or administered in the tail vein (i.v.). The blood samples were collected at 15 and 30 min, 1, 2, 4, 6, 8 and 24 hr after administration in the case of oral administration, and 5 and 30 min, 1, 2, 4, 6, 8 and 24 hr after administration in the case of intravenous administration.

The results are shown in Tables 4 (test compound A), 5 (test compound B) and 6 (test compound C). The Cmax values for i.v. in Tables 4, 5 and 6 show plasma concentration at 5 min after administration.

Cmax by oral administration of test compound A, test compound B and test compound C was 1459.7 ng/mL, 470.8 ng/mL and 2003.0 ng/mL, respectively, and the bioavailability was 104.3%, 75.5% and 80.7%, respectively.

TABLE 4

| Compound A: Mean + SD, n = 3 | | | | |
|---|---|---|---|---|
| Dose | $C_{max}$ (ng/mL) | AUC$_{0-24h}$ (ngh/mL) | AUC$_{0-\infty}$ (ngh/mL) | F[1] (%) |
| 3 mg/kg p.o. | 1459.7 ± 262.7 | 4032.9 ± 501.8 | 4008.2 ± 491.5 | 104.3 ± 12.8 |
| 3 mg/kg i.v. | 2219.9 ± 103.8[2] | 3850 ± 78.4 | 3841.3 ± 77.4 | — |

[1]F (%) = (AUC$_{0-\infty,p.o.}$/AUC$_{0-\infty,i.v.,mean}$) × (Dose$_{i.v.}$/Dose$_{p.o.}$) × 100
[2]C$_{5\ min}$

TABLE 5

| Compound B: Mean + SD, n = 4 | | | | |
|---|---|---|---|---|
| Dose | $C_{max}$ (ng/mL) | AUC$_{0-last}$ (ngh/mL) | AUC$_{0-\infty}$ (ngh/mL) | F[1] (%) |
| 3 mg/kg p.o. | 470.8 ± 154.4 | 1082.8 ± 171.1 | 1105.7 ± 170.8 | 75.5 ± 11.6 |
| 3 mg/kg i.v. | 1604.6 ± 58.3[2] | 1449.8 ± 123.3 | 1464.6 ± 122.3 | — |

[1]F (%) = (AUC$_{0-\infty,p.o.}$/AUC$_{0-\infty,i.v.,mean}$) × (Dose$_{i.v.}$/Dose$_{p.o.}$) × 100
[2]C$_{5\ min}$

TABLE 6

| | | Compound C: Mean ± SD, n = 4 | | |
|---|---|---|---|---|
| Dose | $C_{max}$ (ng/mL) | $AUC_{0\text{-}last}$ (ngh/mL) | $AUC_{0\text{-}\infty}$ (ngh/mL) | $F^{1)}$ (%) |
| 3 mg/kg p.o. | 2003 ± 338.3 | 8192.2 ± 3114.3 | 8434.3 ± 2981.5 | 80.7 ± 28.5 |
| 3 mg/kg i.v. | 4514.7 ± 358.6$^{2)}$ | 10173.6 ± 3012.9 | 10446.3 ± 2852.3 | — |

$^{1)}F (\%) = (AUC_{0\text{-}\infty,p.o.}/AUC_{0\text{-}\infty,i.v.,mean}) \times (Dose_{i.v.}/Dose_{p.o.}) \times 100$
$^{2)}C_{5\,min}$ Pharmacological Experimental Example 6

Evaluation of Intracerebral Transitivity in Rat

The test compound A dissolved in 0.5% aqueous HPMC solution was orally administered at 30 mg/kg, and test compound B and test compound C dissolved in 0.5% aqueous HPMC solution were each orally administered at 3 mg/kg to SD(IGS) rats (Charles River Laboratories Japan). At 1 hr and 4 hr after the administration of the test compound, blood samples were collected, and the brain (cerebral•cerebellum) was isolated. The plasma concentration and intracerebral concentration of each test compound were measured, and the ratio (Kp value) thereof was calculated, based on which the intracerebral transitivity was evaluated.

As a result, it was confirmed that test compound A, test compound B and test compound C were intracerebrally transferred. The Kp value of each test compound at 1 hr and 4 hr after administration was 0.5 and 0.5, respectively, for test compound A, 0.8 and 1.3, respectively, for test compound B and 0.8 and 0.9, respectively, for test compound C.

INDUSTRIAL APPLICABILITY

According to the present invention, a novel therapeutic drug for cerebral infarction can be provided, which suppresses production of plural inflammatory cytokines present in the brain. Particularly, in the present invention, the brain injury volume of a monkey middle cerebral artery permanent occlusion model was noninvasively measured by MRI and detailed neurological deficit (higher brain function) was measured over time as shown in Pharmacological Experimental Example 2, based on which the effectiveness of the above-mentioned compound as a therapeutic drug for cerebral infarction was demonstrated. In general clinical situations, the pathology is measured and scored by evaluation of cerebral infarction by MRI along with incorporation of various indices. In the aforementioned anti-cytokine antibodies and inhibitors, however, measurement in a phenyltetrazolium chloride (hereinafter TTC) stain, and observation of a simple neurological score (Bederson method, paralysis) were only performed with regard to the action on cerebral infarction volume in animal experiments, and accurate clinical prediction of pathological improvement has not been provided. In contrast, a therapeutic drug for cerebral infarction, which is predicted to show a high clinical effect, has been provided in the present invention. The therapeutic drug for cerebral infarction of the present invention can also be provided as a therapeutic drug for inflammatory diseases relating to the brain and spinal cord, such as encephalitis and encephalomyelitis (encephalomyelitis and other diseases caused by nerve inflammation inclusive of infections and autoimmune diseases).

While the present invention has been described in detail by referring to a particular pathology, it is, however, clear to those of ordinary skill in the art that various modifications and changes can be made without departing from the intention and scope of the present invention.

This application is based on a patent application No. 2007-137504 filed in Japan (filing date: May 24, 2007), the contents of which are incorporated in full herein by this reference.

The invention claimed is:

1. A piperazine compound represented by formula <3>

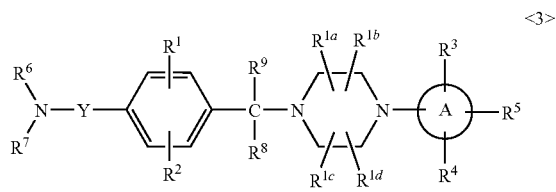

wherein
  $R^1$ and $R^2$ are the same or different and each is hydrogen, halogen, lower alkyl, lower alkoxy, amino, nitro, hydroxy, cyano or amino which is mono- or di-substituted by at least one functional group selected from the group consisting of lower alkyl and lower acyl,
  $R^3$, $R^4$ and $R^5$ are the same or different and each is hydrogen, halogen, lower alkyl, lower alkoxy, nitro, amino, hydroxy, cyano or amino which is mono- or di-substituted by at least one functional group selected from the group consisting of lower alkyl and lower acyl,
  $R^6$ and $R^7$ are the same or different and each is hydrogen, lower alkyl, lower alkyl substituted by 1 to 3 halogens, aralkyl, acyl or lower acyl substituted by 1 to 3 halogens,
  $R^8$ and $R^9$ are the same or different and each is hydrogen or lower alkyl,
  any two of $R^{1a}$-$R^{1d}$ are bonded to each other to form alkylene having a carbon number of 1-2, and other substituents are the same or different and each is hydrogen, lower alkyl, aralkyl or hydroxy lower alkyl,
  Y is a group represented by formula

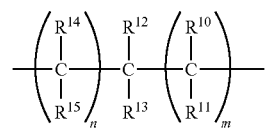

wherein
  $R^{10}$ and $R^{11}$ are the same or different and each is hydrogen or lower alkyl,
  $R^{12}$ and $R^{13}$ are the same or different and each is hydrogen or lower alkyl, or $R^{12}$ and $R^{13}$ are groups that form alkylene in combination,
  $R^{14}$ and $R^{15}$ are the same or different and each is hydrogen or lower alkyl, m is an integer of 0-2, n is an integer of 0-2, and 0≤m+n≤2, and ring A is pyrimidyl, or a pharmaceutically acceptable salt thereof.

2. The piperazine compound according to claim 1, which is N-[1-(4-{[(1S,4S)-5-(pyrimidin-2-yl)-2,5-diazabicyclo[2.2.1]hept-2-yl]methyl}phenyl)cyclopropyl]acetamide or a pharmaceutically acceptable salt thereof.

3. A method of treating a cerebral infarction, the method comprising administering to a subject in need thereof an effective amount of a piperazine compound represented by formula <1>

$$\text{<1>}$$

$$R^6\diagdown N-Y-\underset{R^2}{\underset{|}{\overset{R^1}{\underset{|}{B}}}}-\underset{R^8}{\underset{|}{\overset{R^9}{\underset{|}{C}}}}-N\underset{R^c\ R^d}{\overset{R^a\ R^b}{\diagup\diagdown}}N-\underset{R^4}{\overset{R^3}{A}}-R^5$$

wherein $R^1$ and $R^2$ are the same or different and each is hydrogen, halogen, lower alkyl, lower alkoxy, amino, nitro, hydroxy, cyano or amino which is mono- or di-substituted by at least one functional group selected from the group consisting of lower alkyl and lower acyl, $R^3$, $R^4$ and $R^5$ are the same or different and each is hydrogen, halogen, lower alkyl, lower alkoxy, nitro, amino, hydroxy, cyano or amino which is mono- or di-substituted by at least one functional group selected from the group consisting of lower alkyl and lower acyl, $R^6$ and $R^7$ are the same or different and each is hydrogen, lower alkyl, lower alkyl substituted by 1 to 3 halogens, aralkyl, acyl or lower acyl substituted by 1 to 3 halogens, $R^8$, $R^9$ are the same or different and each is hydrogen or lower alkyl, $R^a$-$R^d$ are the same or different and each is hydrogen, lower alkyl, aralkyl or hydroxy lower alkyl, or any two of $R^a$-$R^d$ are bonded to each other to form alkylene having a carbon number of 1 or 2, Y is a group represented by the formula $$-\left(\underset{R^{15}}{\underset{|}{\overset{R^{14}}{\underset{|}{C}}}}\right)_n-\underset{R^{13}}{\underset{|}{\overset{R^{12}}{\underset{|}{C}}}}-\left(\underset{R^{11}}{\underset{|}{\overset{R^{10}}{\underset{|}{C}}}}\right)_m-$$

wherein $R^{10}$ and $R^{11}$ are the same or different and each is hydrogen or lower alkyl, $R^{12}$ and $R^{13}$ are the same or different and each is hydrogen or lower alkyl, or $R^{12}$ and $R^{13}$ are groups that form alkylene in combination, $R^{14}$ and $R^{15}$ are the same or different and each is hydrogen or lower alkyl, and m is an integer of 0-2, n is an integer of 0-2 and 0≤m+n≤2, ring A is pyrimidiyl, and ring B is phenyl, and wherein any two of $R^a$-$R^d$ are bonded to each other to form alkylene having a carbon number of 1 or 2, or a pharmaceutically acceptable salt thereof.

4. The method of treating a cerebral infarction according to claim 3, wherein the piperazine compound is N-[1-(4-{[(1S,4S)-5-(pyrimidin-2-yl)-2,5-diazabicyclo[2.2.1]hept-2-yl]methyl}phenyl)cyclopropyl]acetamide, or a pharmaceutically acceptable salt thereof.

5. The method according to claim 3, wherein the piperazine compound is a compound of formula <1> wherein $R^1$ and $R^2$ are hydrogen, $R^3$, $R^4$ and $R^5$ are the same or different and each is hydrogen, halogen or lower alkoxy, $R^6$ and $R^7$ are the same or different and each is hydrogen or acyl, $R^8$ and $R^9$ are the same or different and each is hydrogen or lower alkyl, $R^{10}$ and $R^{11}$ are hydrogen, $R^{14}$ and $R^{15}$ are hydrogen, any two of $R^a$, $R^b$, $R^c$ and $R^d$ are bonded to each other to form alkylene having a carbon number of 1 and other groups are hydrogen, ring A is pyrimidyl, and ring B is phenyl, or a pharmaceutically acceptable salt thereof.

6. The method according to claim 3, wherein the piperazine compound is a compound of formula <1> wherein $R^{12}$ and $R^{13}$ are groups that form alkylene in combination, or a pharmaceutically acceptable salt thereof.

7. The method according to claim 3, wherein the cerebral infarction is atherothrombotic brain infarction, lacunar infarction or cardioembolic stroke.

8. The piperazine compound according to claim 1, which is represented by formula <5>

$$\text{<5>}$$

$$\underset{R^6}{\overset{H}{\diagdown}}N-\underset{R^2}{\underset{|}{\overset{R^1}{\diagup\diagdown}}}-\underset{H}{\underset{|}{\overset{H}{\underset{|}{C}}}}-N\underset{R^{1c}\ R^{1d}}{\overset{R^{1a}\ R^{1b}}{\diagup\diagdown}}N-\underset{R^4}{\overset{R^3}{\diagup\diagdown}}-R^5$$

wherein $R^1$ and $R^2$ are the same or different and each is hydrogen, halogen, lower alkyl, lower alkoxy, amino, nitro, hydroxy, cyano or amino which is mono- or di-substituted by at least one functional group selected from the group consisting of lower alkyl and lower acyl, $R^3$, $R^4$ and $R^5$ are the same or different and each is hydrogen, halogen, lower alkyl, lower alkoxy, nitro, amino, hydroxy, cyano or amino which is mono- or di-substituted by at least one functional group selected from the group consisting of lower alkyl and lower acyl, $R^6$ is acyl or lower acyl substituted by 1 to 3 halogens, and any two of $R^{1a}$-$R^{1d}$ are bonded to each other to form alkylene having a carbon number of 1-2, and other substituents are the same or different and each is hydrogen, lower alkyl, aralkyl or hydroxy lower alkyl, or a pharmaceutically acceptable salt thereof.

9. The method of treating a cerebral infarction according to claim 3, wherein the piperazine compound is also effective for suppressing production of cytokines TNF-α, IL-1β and IL-6, and chemokine MCP-1, and promoting production of IL-10.

* * * * *

UNITED STATES PATENT AND TRADEMARK OFFICE
CERTIFICATE OF CORRECTION

PATENT NO. : 8,835,631 B2
APPLICATION NO. : 12/601609
DATED : September 16, 2014
INVENTOR(S) : Haruto Nakagawa et al.

Page 1 of 1

It is certified that error appears in the above-identified patent and that said Letters Patent is hereby corrected as shown below:

In the Claims

Column 36, lines 33-43 in Claim 8,

"
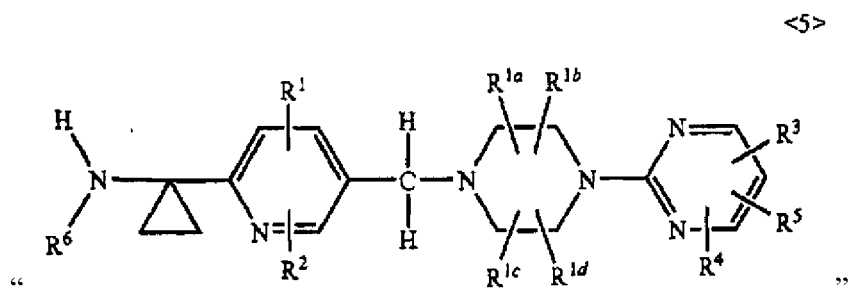
"

should read

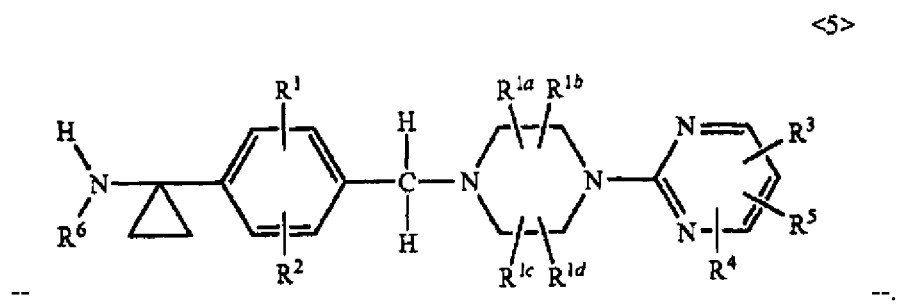

--                                                                                  --.

Signed and Sealed this
Twenty-first Day of April, 2015

Michelle K. Lee
*Director of the United States Patent and Trademark Office*